(12) United States Patent
Koshida et al.

(10) Patent No.: US 10,716,968 B2
(45) Date of Patent: Jul. 21, 2020

(54) INFORMATION PROCESSING SYSTEM

(71) Applicant: SONY CORPORATION, Tokyo (JP)

(72) Inventors: Osamu Koshida, Saitama (JP); Tamotsu Ishii, Tokyo (JP); Yasuyuki Suki, Tokyo (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 15/528,557

(22) PCT Filed: Aug. 28, 2015

(86) PCT No.: PCT/JP2015/074361
§ 371 (c)(1),
(2) Date: May 22, 2017

(87) PCT Pub. No.: WO2016/092912
PCT Pub. Date: Jun. 16, 2016

(65) Prior Publication Data
US 2017/0266492 A1  Sep. 21, 2017

(30) Foreign Application Priority Data
Dec. 11, 2014  (JP) ................. 2014-250839

(51) Int. Cl.
*A63B 24/00* (2006.01)
*G16H 20/30* (2018.01)
(Continued)

(52) U.S. Cl.
CPC ...... *A63B 24/0006* (2013.01); *A63B 24/0062* (2013.01); *A63B 69/00* (2013.01);
(Continued)

(58) Field of Classification Search
None
See application file for complete search history.

(56) References Cited

U.S. PATENT DOCUMENTS

| 6,811,516 B1* | 11/2004 | Dugan | G06F 19/3418 482/8 |
| 2005/0172311 A1* | 8/2005 | Hjelt | A61B 5/1112 725/10 |

(Continued)

FOREIGN PATENT DOCUMENTS

| JP | 2001-299980 A | 10/2001 |
| JP | 2003-175139 A | 6/2003 |

(Continued)

OTHER PUBLICATIONS

"Which one do you choose, "UP" or "Fitbit One"? Life Log Management with iPhone! Life Improvement Plans", Mac People, 2013, pp. 93-103.

(Continued)

*Primary Examiner* — Herve-Louis Y Assouman
(74) *Attorney, Agent, or Firm* — Chip Law Group

(57) ABSTRACT

[Object] To propose a novel and improved program and information processing system that can perform feedback in accordance with a history of exercise of the user. [Solution] Provided is a program causing a computer to function as an acquirer configured to acquire information indicating an exercise state of a user, a storage controller configured to allow the information indicating the exercise state acquired by the acquirer to be stored, and an output controller configured to allow provision information that is to be provided to the user to be output, the provision information being generated on the basis of a history of the information indicating the exercise state stored by the storage controller.

14 Claims, 15 Drawing Sheets

(51) Int. Cl.
  *G06F 16/2458* (2019.01)
  *A63B 71/06* (2006.01)
  *A63B 69/00* (2006.01)

(52) U.S. Cl.
  CPC .......... *A63B 71/06* (2013.01); *G06F 16/2462* (2019.01); *G16H 20/30* (2018.01); *A63B 2024/0068* (2013.01)

(56) References Cited

U.S. PATENT DOCUMENTS

| | | | | |
|---|---|---|---|---|
| 2007/0118043 | A1* | 5/2007 | Oliver | A61B 5/0245 600/519 |
| 2008/0051919 | A1 | 2/2008 | Sakai et al. | |
| 2008/0236369 | A1* | 10/2008 | Sasaki | A63B 71/0686 84/612 |
| 2009/0271496 | A1* | 10/2009 | Nakamura | G06Q 30/02 709/217 |
| 2010/0160014 | A1* | 6/2010 | Galasso | A63B 24/0021 463/6 |
| 2012/0015779 | A1* | 1/2012 | Powch | A61B 5/02055 482/9 |
| 2014/0172132 | A1 | 6/2014 | Ura | |

FOREIGN PATENT DOCUMENTS

| | | |
|---|---|---|
| JP | 2007-075172 A | 3/2007 |
| JP | 2007-130356 A | 5/2007 |
| JP | 2009-078134 A | 4/2009 |
| JP | 2011-189014 A | 9/2011 |
| JP | 2013-146557 A | 8/2013 |
| JP | 2013-536507 A | 9/2013 |
| JP | 2013-543156 A | 11/2013 |
| JP | 2014-014701 A | 1/2014 |
| JP | 2014-168685 A | 9/2014 |

OTHER PUBLICATIONS

Resona Hikawa, "Features of Apple Watch, Health & Fitness 6, Keep Recording Activities and Analyze the Workout", Mac Fan, Nov. 2014 pp. 56-57.
"Which one do you choose, "UP" or "Fitbit One"? Life Log Management with iPhone! Life Improvement Plans", [Special Feature 4] iPhone People, Mac People, Aug. 2013, pp. 94-103.
Hikawa Resona, "Health & Fitness 6, Keep Recording Activities and Analyze the Workout", Health & Fitness 6, Mac Fan, Nov. 2014, pp. 56-57.
Office Action for CN Patent Application No. 2016563549, dated May 21, 2019, 17 pages of Office Action and 16 pages of English Translation.
Uchiyama Hideki, "Which Do You Select, [UP] or [Fitbit One]", Life Log Management by iPhone, Mac People, vol. 19, No. 8, Aug. 2013, 12 pages.
Risona Nagakawa, "Extremely Large Volume, I Teach Everything from Knowledge Necessary for Purchasing to Daily Using Method", Both Are Wanted, iPhone 6&6 Plus Apple Watch, MacFan, vol. 22, No. 11, May 23, 2019, 03 pages.
Hideki Uchiyama, "Which of [UP] or [Fitbit One] Do You Select ? Life Log Management by iPhone Life Improvement Plan", iPhone People, Macpeople, vol. 19, No. 8, Aug. 2013, pp. 94-103.
Resona Hikawa, "Especially Extra Large Volume !, I Teach Everything from Knowledge Required for Purchase to Daily Usage !, Want Both !, iPhone 6&6 Plus Apple Watch", Health Fitness, MacFan, vol. 22, No. 11, Nov. 2014, pp. 56-57.
Office Action for JP Patent Application No. 2016-563549, dated Dec. 10, 2019, 06 pages of Office Action and 07 pages of English Translation.

* cited by examiner

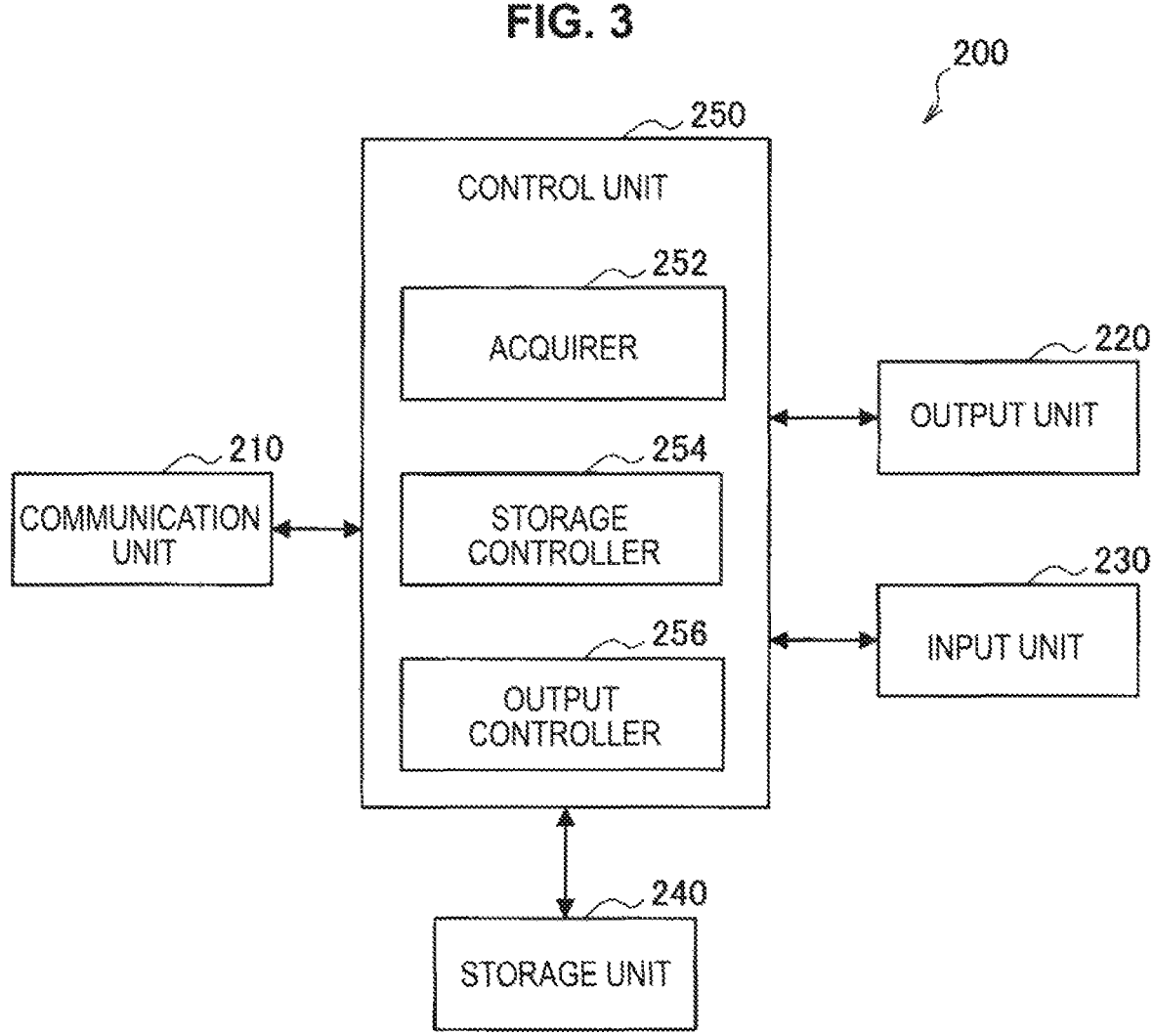
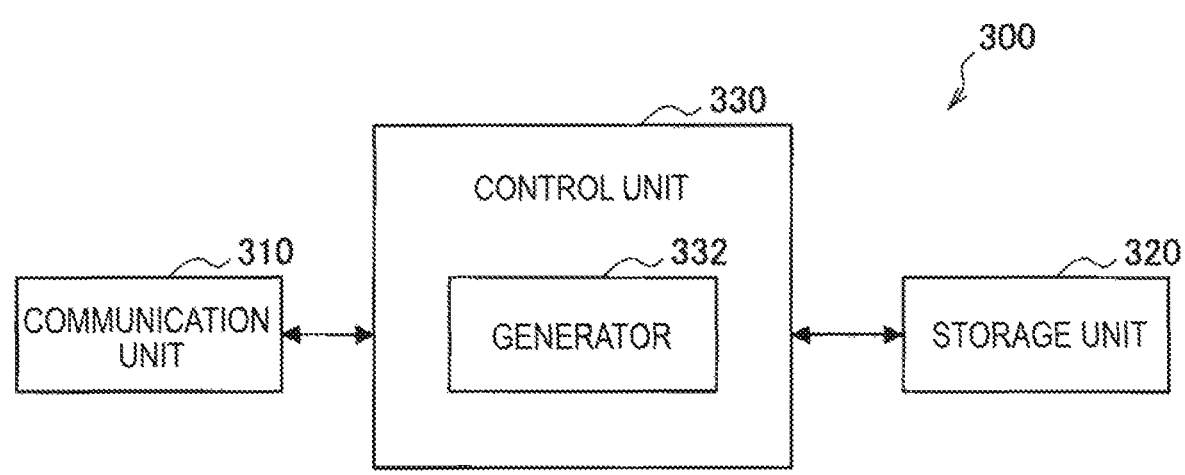

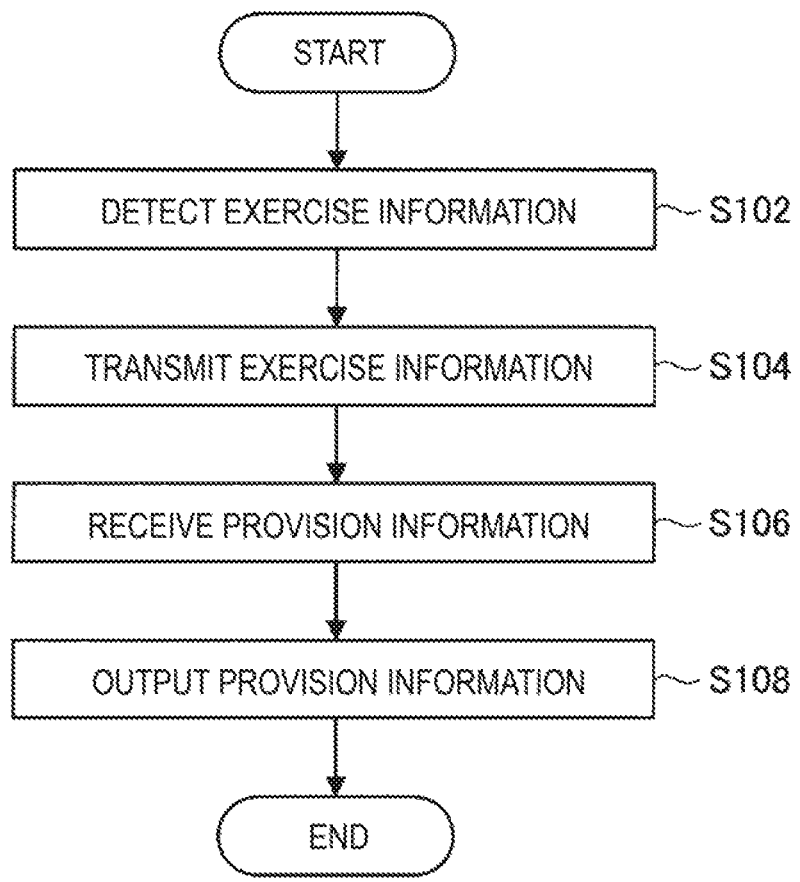

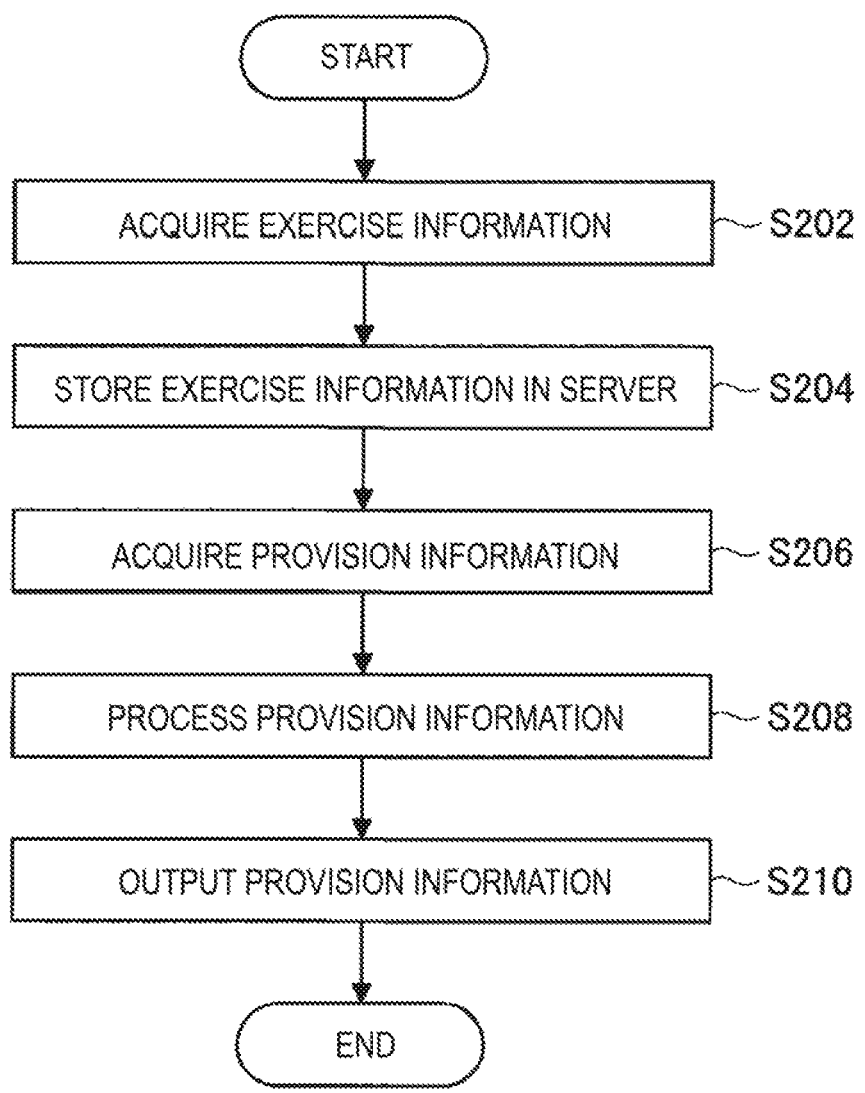

INFORMATION PROCESSING SYSTEM

CROSS REFERENCE TO RELATED APPLICATIONS

This application is a U.S. National Phase of International Patent Application No. PCT/JP2015/074361 filed on Aug. 28, 2015, which claims priority benefit of Japanese Patent Application No. JP 2014-250839 filed in the Japan Patent Office on Dec. 11, 2014. Each of the above-referenced applications is hereby incorporated herein by reference in its entirety.

TECHNICAL FIELD

The present disclosure relates to a program and an information processing system.

BACKGROUND ART

In recent years, there has been demand not only for devices with high performance and high functionality but also for a technology for providing better user experience. For example, devices such as a smartphone or a wearable device have been widely used to provide better services for users' daily lives since the users can carry the devices with ease. As an example, a technology enabling the provision of better sports experience has been developed.

For example, Patent Literature 1 below has disclosed a technology in which light, vibration, or the like indicating heartbeat information measured by a mounted device is output, enabling a user on which the device is mounted or a third party to identify the user's heartbeat information while keeping exercising.

CITATION LIST

Patent Literature

Patent Literature 1: JP 2007-130356A

DISCLOSURE OF INVENTION

Technical Problem

However, in the technology described in Patent Literature 1 above, it is only possible to identify the state during exercise. Therefore, for example, it is difficult for the user to receive feedback taking into consideration whether the user is in good or bad condition compared to a history of past exercise, the degree of improvement, or the like. Thus, the present disclosure proposes a novel and improved program and information processing system that can perform feedback in accordance with a history of exercise of the user.

Solution to Problem

According to the present disclosure, there is provided a program causing a computer to function as: an acquirer configured to acquire information indicating an exercise state of a user; a storage controller configured to cause the information indicating the exercise state acquired by the acquirer to be stored; and an output controller configured to cause provision information that is to be provided to the user to be output, the provision information being generated on a basis of a history of the information indicating the exercise state stored by the storage controller.

According to the present disclosure, there is provided an information processing system including: a wearable device that is worn by a user; a server; and a terminal device configured to perform communication with the wearable device and the server. The wearable device includes a sensor unit configured to detect information indicating an exercise state of the user, and an output unit configured to output provision information generated by the server. The server includes a storage unit configured to store information indicating the exercise state, and a generator configured to generate the provision information, which is to be provided to the user, on a basis of a history of the information indicating the exercise state stored in the storage unit. The terminal device includes an acquirer configured to acquire the information indicating the exercise state detected by the wearable device, a storage controller configured to cause the server to store the information indicating the exercise state acquired by the acquirer, and an output controller configured to cause the output unit to output the provision information generated by the generator.

Advantageous Effects of Invention

According to the present disclosure, it is possible to perform feedback in accordance with a history of exercise of a user as described above. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 3 is a block diagram illustrating an exemplary logical configuration of a smartphone according to the present embodiment.

FIG. 4 is a block diagram illustrating an exemplary logical configuration of a server according to the present embodiment.

FIG. 5 is a flowchart illustrating an exemplary flow of a provision information output process performed by the headset according to the present embodiment.

FIG. 6 is a flowchart illustrating an exemplary flow of a provision information output process performed by the smartphone according to the present embodiment.

MODE(S) FOR CARRYING OUT THE INVENTION

Figure 1:
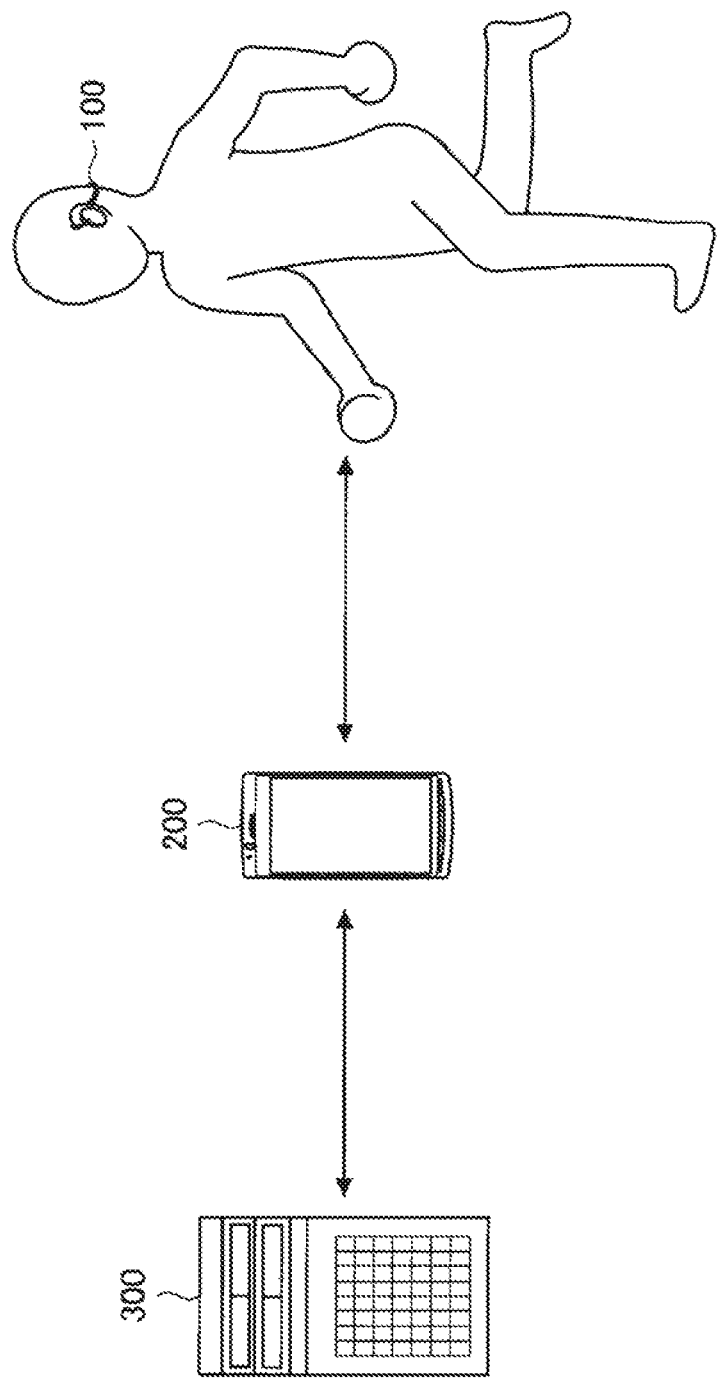
FIG. 1 is a view illustrating an overview of a training support system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description will be given in the following order.
1. Overview
2. Configuration
2-1. Exemplary configuration of headset
2-2. Exemplary configuration of smartphone
2-3. Exemplary configuration of server
3. Operation processes
4. Hardware configuration
4-1. First exemplary configuration
4-2. Second exemplary configuration
5. Summary 1. Overview First, an overview of a training support system 1 according to an embodiment of the present disclosure is described below with reference to FIG. 1.

FIG. 1 is a view illustrating an overview of a training support system 1 according to an embodiment of the present disclosure. As shown in FIG. 1, the training support system 1 according to the present embodiment includes a wearable device 100, a terminal device 200, and a server 300.

The wearable device 100 is a device that is worn by a user. The wearable device 100 acquires various information from the user and transmits the acquired information to the terminal device 200. The wearable device 100 also outputs information received from the terminal device 200 to the user. In the example shown in FIG. 1, the wearable device 100 is a headset. For example, the user wears the headset 100 to listen to music while playing a sport or to receive feedback in accordance with exercise performed by them. Information to be fed back to the user may be generated by the server 300 and may also be detected in real time by the headset 100. In the following description, the information to be fed back to the user is also referred to as "provision information". The headset 100 preferably has a waterproof structure. The wearable device 100 may also be realized as devices of various types, other than a headset, such as a glasses-like device, a contact lens-like device, or a necklace-like device.

The terminal device 200 is a device that relays communication between the headset 100 and the server 300. For example, the terminal device 200 transmits information received from the headset 100 to the server 300. The terminal device 200 also transmits information received from the server 300 to the headset 100. The terminal device 200 may also receive information input by the user and output information to the user. In the example shown in FIG. 1, the terminal device 200 is a smartphone. The user allows the smartphone 200 to output provision information associated with exercise that they have performed in the past or performs setting as to which provision information the smartphone 200 outputs. The terminal device 200 may also be realized as devices of various types, other than a smartphone, such as a tablet terminal, a mobile phone, a personal computer (PC), or a notebook PC.

The server 300 is a device that accumulates information associated with the user and generates provision information to be fed back to the user in accordance with the accumulated information. The server 300 accumulates information received from the smartphone 200 and transmits information generated in accordance with the accumulated information to the smartphone 200. For example, the server 300 accumulates information associated with exercise performed by the user as a history and generates information for improvement in accordance with the history. The information generated by the server 300 is output to the user through the headset 100 or the smartphone 200. The server 300 may be realized as a single device as shown in FIG. 1 and may also be realized as a group of devices that forms a so-called cloud.

In this manner, the training support system 1 can not only feed information associated with exercise, which the user is performing, back to them in real time, but can also perform feedback associated with a history of past exercise. Therefore, the user can receive feedback which takes into consideration whether the user is in good or bad condition compared to the history of past exercise, the degree of improvement, or the like.

Although the following description will be given with reference to running (jogging) as an example of the sport played by the user, it is considered that the present technology can be applied to a variety of sports. For example, the present technology can be applied to a variety of sports such as swimming, baseball, tennis, horse riding, skiing, rowing, shooting, or martial arts.

An overview of the training support system 1 according to the present embodiment has been described above.

2. Configuration

Exemplary configurations of the headset 100, the smartphone 200, and the server 300 according to the present embodiment are sequentially described below with reference to FIGS. 2 to 4.

[2-1. Exemplary Configuration of Headset]

Figure 2:
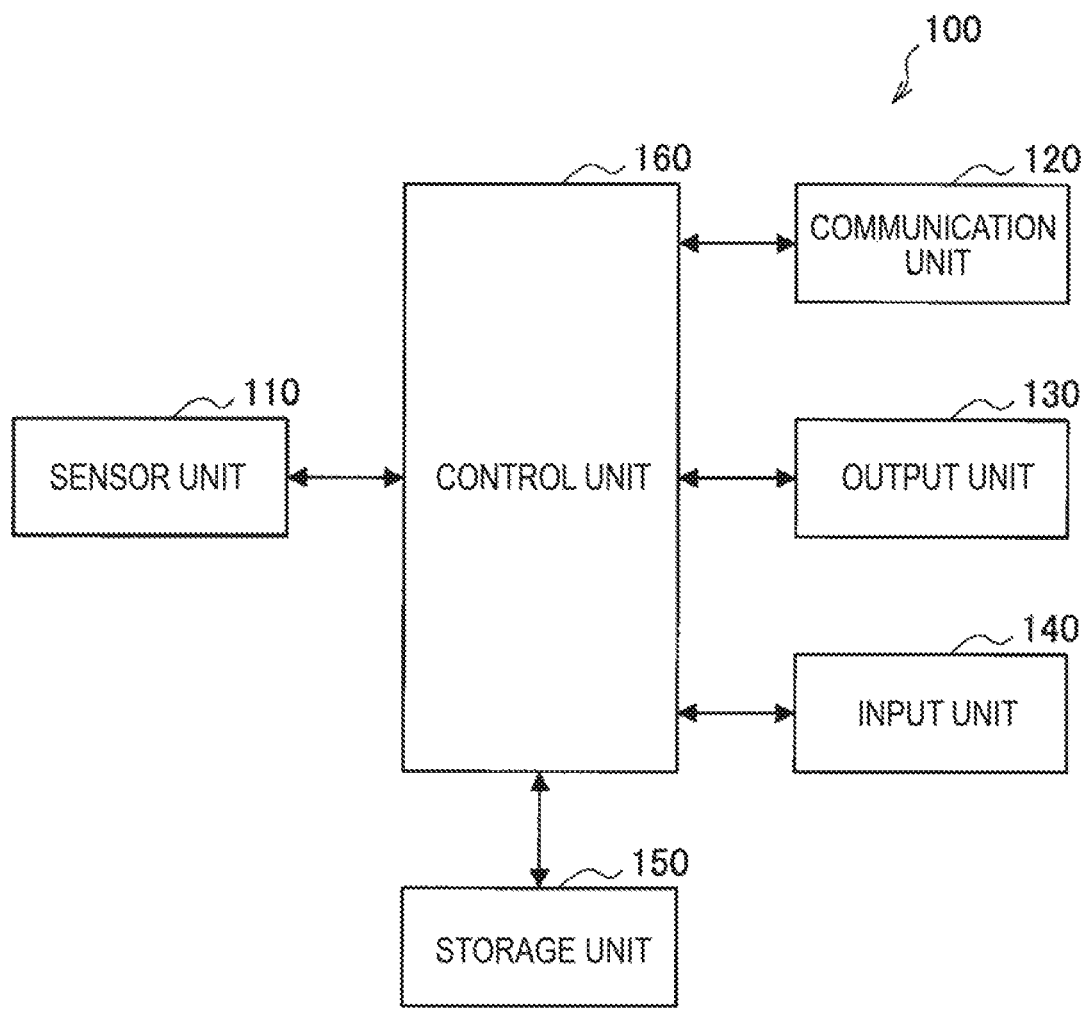
FIG. 2 is a block diagram illustrating an exemplary logical configuration of a headset according to the present embodiment.

FIG. 2 is a block diagram illustrating an exemplary logical configuration of the headset 100 according to the present embodiment. As shown in FIG. 2, the headset 100 includes a sensor unit 110, a communication unit 120, an output unit 130, an input unit 140, a storage unit 150, and a control unit 160.

(1) Sensor Unit 110

The sensor unit 110 has a function to detect information indicating the user's exercise state. In the following description, the information indicating the user's exercise state is referred to as "exercise information". For example, the sensor unit 110 includes at least one of an inertial sensor or a biological sensor and the exercise information is detected by at least one of the inertial sensor or the biological sensor. The inertial sensor may include at least one of a gyro sensor or an acceleration sensor. Exercise information detected by the inertial sensor includes the acceleration, vibration, movement, and posture of the user who wears the headset 100. The biological sensor may include at least one of a heartbeat sensor, a body temperature sensor, or a sweat sensor. Exercise information detected by the biological sensor includes the heart rate, the body temperature, and the amount of sweat of the user who wears the headset 100.

The exercise information may include a variety of other information. For example, location information or altitude information is also included in the exercise information for a sport such as jogging or mountain climbing where the result of exercise is reflected in a movement distance or a height difference. Therefore, the sensor unit 110 may include a global positioning system (GPS) module that can acquire location information, an altitude sensor (barometric sensor) that can acquire altitude information, or the like.

The sensor unit 110 may also include a pedometer that can acquire the number of steps taken, a compass that can acquire geographic direction information, a camera that can capture an image of the surroundings of the user, or the like.

The sensor unit 110 may also have a function to convert raw data detected by various sensors into information corresponding to the sport. For example, for running, the sensor unit 110 may calculate the user's stride length from the relationship between the number of steps and a distance of travel in the past or may calculate a distance of travel using the calculated stride length and the number of steps detected by the pedometer. The sensor unit 110 also calculates a speed and lap time from the distance of travel, calculates a height difference from the altitude information, or calculates the intensity of exercise from the speed and the height difference. The sensor unit 110 may also calculate other information such as the number of steps, a pitch, a stride, a pace, a travel path, calorie consumption, a geographic direction, the body's posture or direction, or the like. The sensor unit 110 outputs the exercise information after conversion.

(2) Communication Unit 120

The communication unit 120 is a communication interface that relays wired or wireless communication of the headset 100 with other devices. For example, the communication unit 120 transmits exercise information detected by the sensor unit 110 to the smartphone 200. The communication unit 120 receives provision information from the smartphone 200.

(3) Output Unit 130

The output unit 130 has a function to output provision information, which is to be provided to the user, as audio, vibration, video, images or the like. The output unit 130 according to the present embodiment may be realized as an audio output device. Output of the provision information as audio is useful for the user keeping focused on exercise, taking into consideration the difficulty in viewing or manipulating the screen while exercising.

(4) Input Unit 140

The input unit 140 has a function to receive a user manipulation. For example, the input unit 140 receives a manipulation for adjusting the volume of audio output by the output unit 130. The input unit 140 may also have a microphone and may receive an audio input.

(5) Storage Unit 150

The storage unit 150 has a function to store a variety of information. For example, the storage unit 150 stores exercise information detected by the sensor unit 110. The storage unit 150 also stores information received by the communication unit 120.

(6) Control Unit 160

The control unit 160 has a function to control the overall internal operation of the headset 100.

For example, the control unit 160 controls the output unit 130 such that it outputs (speaks) exercise information detected by the sensor unit 110. This allows the user to receive feedback of their speed, lap time, heart rate, or the like in real time. The control unit 160 may also control the content of the exercise information that is to be output and/or the output timing of the exercise information in accordance with a setting performed by the user. For example, the control unit 160 may restrict the content of the exercise information to be output to the distance of travel or the like or may set the unit of the distance of travel to kilometers in accordance with the user setting. The control unit 160 may also set the output timing of the exercise information at intervals of 10 minutes or the like in accordance with the user setting. Feeding exercise information back in accordance with the user setting in this manner allows the user to receive their needed exercise information at appropriate timings during exercise.

For example, the control unit 160 controls the output unit 130 such that it outputs provision information received by the communication unit 120. The provision information is generated in accordance with exercise information acquired and accumulated in the past as described later. Therefore, while exercising, the user can receive coaching or the like in accordance with a history of their past exercise.

For example, the control unit 160 may control the output unit 130 such that it outputs provision information further on the basis of real-time exercise information detected by the sensor unit 110. For example, when the sport played by the user is running, the control unit 160 may output information instructing that the user's speed be increased or decreased in accordance with the user's speed. For example, the control unit 160 may output provision information for modifying the user's form to a suitable one in accordance with the user's body posture. This allows the user to receive provision information suited to the exercise, which they are performing, at appropriate timings during the exercise.

Here, the control unit 160 may first allow the storage unit 150 to store provision information received from the smartphone 200 and may then allow the provision information stored in the storage unit 150 to be output. In this case, after the provision information is stored in the headset 100, the user can perform exercise by wearing the headset 100 alone without carrying the smartphone 200.

For example, the control unit 160 may record information, which the user has input to the input unit 140, in the storage unit 150. Specifically, the control unit 160 may record the user's voice as a voice memo in the storage unit 150. Here, the control unit 160 may record the voice memo and position information, indicating a position where the voice memo is recorded, in association with each other. Similarly, the control unit 160 may record a playback history indicating a history of played music in the storage unit 150. Here, the control unit 160 may record the playback history and position information, indicating a position where the playback history is recorded, in association with each other.

In addition, the control unit 160 may perform various output control. For example, the control unit 160 may control the output unit 130 and the input unit 140 such that they perform audio output and audio input associated with voice communication such as telephoning, Voice over Internet Protocol (VoIP) or Voice over LTE (VoLTE) that is performed by the smartphone 200. In addition, the control unit 160 may allow the output unit 130 to output guidance audio for a running course in accordance with the geographic direction. The control unit 160 may also record a captured image as a life log in the storage unit 150.

Further, the control unit 160 may control the communication unit 120 such that it transmits exercise information detected by the sensor unit 110 to the smartphone 200. The control unit 160 may first allow the storage unit 150 to store the detected exercise information in the storage unit 150 and may then allow the communication unit 120 to transmit the exercise information stored in the storage unit 150. In this case, the user can perform exercise by wearing the headset 100 alone without carrying the smartphone 200.

The smartphone 200 may also have all or part of the functions of the headset 100. When the smartphone 200 has all functions of the headset 100, the training support system 1 may not include the headset 100. In this case, the smartphone 200 transmits exercise information detected by a sensor unit included in the smartphone 200 to the server 300 and provides provision information generated by the server 300 to the user via earphones or the like.

An exemplary configuration of the headset 100 according to the present embodiment has been described above.

[2-2. Exemplary Configuration of Smartphone]

FIG. 3 is a block diagram illustrating an exemplary logical configuration of the smartphone 200 according to the present embodiment. As shown in FIG. 3, the smartphone 200 includes a communication unit 210, an output unit 220, an input unit 230, a storage unit 240, and a control unit 250.

(1) Communication Unit 210

The communication unit 210 is a communication interface that relays wired or wireless communication of the smartphone 200 with other devices. For example, the communication unit 210 receives exercise information from the headset 100 and transmits the received exercise information to the server 300. The communication unit 210 transmits provision information received from the server 300 to the headset 100.

(2) Output Unit 220

The output unit 220 has a function to output, as audio, vibration, video, images or the like, provision information that is to be provided to the user. The output unit 130 according to the present embodiment may be realized, for example, as a display device.

(3) Input Unit 230

The input unit 230 has a function to receive a user manipulation. For example, the input unit 230 may receive a manipulation associated with provision information, which is to be provided to the user, such as a manipulation for selecting a training plan. The input unit 230 may also receive a manipulation for performing setting associated with the content of exercise information which is to be fed back to the user and/or with the output timing of the exercise information.

(4) Storage Unit 240

The storage unit 240 has a function to store a variety of information. For example, the storage unit 240 stores exercise information received from the headset 100. The storage unit 240 also stores provision information received from the server 300.

(5) Control Unit 250

The control unit 250 has a function to control the overall internal operation of the smartphone 200. The control unit 250 has functions as an acquirer 252, a storage controller 254, and an output controller 256 as shown in FIG. 3.

(5-1) Acquirer 252

The acquirer 252 has a function to acquire exercise information indicating the user's exercise state. The acquirer 252 may acquire exercise information from a wearable device which is worn by the user. For example, the acquirer 252 acquires exercise information from the headset 100 through the communication unit 210. The acquirer 252 may also acquire exercise information from a wearable sensor device, other than the headset 100, which is worn by the user through the communication unit 210. The smartphone 200 may have a sensor unit similar to the sensor unit 110 described above and the acquirer 252 may acquire exercise information from the sensor unit.

(5-2) Storage Controller 254

The storage controller 254 has a function to allow exercise information acquired by the acquirer 252 to be stored. For example, the storage controller 254 transmits exercise information acquired by the acquirer 252 to the server 300 through the communication unit 210 and allows the server 300 to store the exercise information. The storage controller 254 may first allow the storage unit 240 to store exercise information acquired by the acquirer 252 and may then allow the exercise information to be transmitted to the server 300.

(5-3) Output Controller 256

The output controller 256 has a function to allow provision information, which is to be provided to the user, to be output, the provision information being generated on the basis of a history of information indicating the exercise state stored by the storage controller 254. The output controller 256 may allow the headset 100 to output the provision information through the communication unit 210 and may also allow the output unit 220 to output the provision information. The provision information is generated by the server 300 as described later. The output controller 256 may perform control to output a variety of information.

The output controller 256 may allow the output unit 220 to output a variety of information.

For example, the output controller 256 may perform control to output a setting screen associated with provision information that is to be provided to the user. For example, the output controller 256 may allow a screen for selecting a training plan to be displayed. Information indicating the selected training plan is transmitted to the headset 100 through the communication unit 210. The output controller 256 may also allow a setting screen to be displayed, the setting screen being used to perform setting associated with the content of exercise information which is to be fed back to the user and/or with the output timing of the exercise information.

For example, the output controller 256 may display a screen for supporting the user who is exercising. Specifically, the output controller 256 may allow exercise information to be output in real time.

For example, the output controller 256 may perform control to output information associated with exercise performed by the user. Specifically, the output controller 256 may allow the output unit 220 to output information indicating the results of the exercise of the user. The output controller 256 may also allow the output unit 220 to output a history of exercise information accumulated in the server 300 in a visual form of statistical information such as a graph or a table. In addition, the output controller 256 may output a voice memo in association with position information indicating a position where the voice memo is recorded. Specifically, the output controller 256 may display the recorded position of the voice memo on a map. The same applies to a playback history of music.

The output controller 256 may allow the headset 100 to output a variety of information.

For example, the output controller 256 may control the tempo of music that is played in accordance with a target exercise state. For example, the output controller 256 speeds up the tempo when the target heart rate is high and slows down the tempo when the target heart rate is low. Specifically, when the sport played by the user is running, the output controller 256 speeds up the tempo when the target speed is high and slows down the tempo when the target speed is low. Here, for tempo control, the output controller 256 may change the tempo without changing a music file being played and may also change the music file being played. In addition, a target exercise state may be included in the provision information generated by the server 300. Since the tempo of music that is played is controlled in accordance with a target exercise state, entrainment occurs such that the user's feet become unconsciously in tune with the tempo of the music, allowing the user to be naturally encouraged to transit to the target exercise state. For example, this reduces the user's stress compared to when the user is instructed in an imperative way to change their exercise state. In addition, the output controller 256 may control the tempo of music that is played in accordance with the user's exercise state. For example, the output controller 256 speeds up the tempo when the user's heart rate is high and slows down the tempo when the heart rate is low. In this case, the user can more fully immerse themselves in the exercise since the output from the user (exercise) and the input to the user (music) harmonize with each other. The music file that is played by the output controller 256 may be stored in the storage unit 240 of the smartphone 200 and may also be stored in the storage unit 150 of the headset 100.

For example, the output controller 256 may process provision information, which is to be provided, in accordance with a user instruction. Specifically, the output controller 256 may process a variable part of the provision information generated by the server 300 in accordance with a user instruction. For example, when a training plan generated by the server 300 includes walking and jogging, the output controller 256 changes the travel distance, travel time, pace, and the like of walking and jogging in accordance with a user instruction. The user can change the provision information as they desire since the provision information is processed in accordance with a user instruction.

In addition, when the output controller 256 allows the headset 100 to output the provision information, the output controller 256 may transmit the provision information to the headset 100 through the communication unit 210 after converting the provision information into an audio signal. Of course, the processing of conversion into an audio signal may be performed at the headset 100.

(5-4) Others

The control unit 250 has a function to process a variety of information. For example, the control unit 250 may perform an audio recognition process on audio spoken by the user that has been acquired by the headset 100. The control unit 250 may also perform an image recognition process on an image captured by the headset 100. In addition, the control unit 250 may post information associated with the user's exercise to a social networking service (SNS). These processes may be performed by the control unit 250 and all or part thereof may be performed by the server 300.

The headset 100 may have all or part of the functions of the smartphone 200. When the headset 100 has all functions of the smartphone 200, the training support system 1 may not include the smartphone 200. In this case, the headset 100 performs communication directly with the server 300 and provides provision information to the user. In this case, the headset 100 transmits detected exercise information to the server 300 and provides provision information generated by the server 300 to the user.

In a specific example where the headset 100 has a part of the functions of the smartphone 200, the headset 100 may have the function of the output controller 256 to control the tempo of music that is played. In this case, when a music file stored in the storage unit 150 is played, the headset 100 may control the tempo of the music that is played in accordance with a target exercise state.

An exemplary configuration of the smartphone 200 according to the present embodiment has been described above.

[2-3. Exemplary Configuration of Server]

FIG. 4 is a block diagram illustrating an exemplary logical configuration of the server 300 according to the present embodiment. As shown in FIG. 4, the server 300 includes a communication unit 310, a storage unit 320, and a control unit 330.

(1) Communication Unit 310

The communication unit 310 is a communication interface that relays wired or wireless communication of the server 300 with other devices. For example, the communication unit 310 receives exercise information from the smartphone 200. The communication unit 310 also transmits provision information generated by a generator 332, which is described below, to the smartphone 200. The communication unit 310 may also perform communication with devices such as other servers.

(2) Storage Unit 320

The storage unit 320 has a function to store a variety of information. For example, the storage unit 320 stores exercise information received from the smartphone 200. The storage unit 320 may also store a variety of information used by the generator described below. For example, the storage unit 320 may store a database of training plans.

(3) Control Unit 330

The control unit 330 has a function to control the overall internal operation of the server 300. As shown in FIG. 4, the control unit 330 has a function as the generator 332.

The generator 332 has a function to generate provision information, which is to be provided to the user, on the basis of a history of exercise information of the user that is stored in the storage unit 320 after being received from the smartphone 200. The generator 332 may generate provision information in accordance with ambient environments (such as a geographical environment, a human environment, and events) of the user in addition to the history of exercise information.

For example, the provision information may be generated further on the basis of a sport played by the user. For example, the generator 332 may generate different provision information from the same history of exercise information in accordance with whether the sport played by the user is running or walking.

For example, the provision information may include advice for the sport played by the user. For example, the provision information may include a training plan for improvement in the sport and may also include coaching for form improvement or the like. This provision information may be information that is provided while the user is exercising. For example, when the sport played by the user is running, the provision information may be information for feeding back a target exercise state, such as a lap time to achieve, as appropriate. The provision information may also be information that is provided before exercise. For example, the provision information may be information for instructing that warm-up be performed before exercise or for presenting the overall picture of a training plan. The provision information may also be information that is provided after exercise. For example, the provision information may be information for presenting the difference between a target and a result of the user's exercise. In this manner, the user is provided with provision information including advice for a sport played by them. Therefore, the user can do training suitable for their exercise ability, achieving steady improvement.

For example, the provision information may include information indicating an event associated with a sport played by the user. For example, when the sport played by the user is running, the provision information may be information of marathon races and may also be information of classes for improving running techniques. In this manner, the user is provided with provision information including information indicating an event associated with a sport played by them. Therefore, the user can easily participate in events held around them.

For example, the provision information may include information indicating products associated with a sport played by the user. For example, when the sport played by the user is running, the provision information may be information of running shoes and may also be information of a sale on running wear. In this manner, the user is provided with provision information including information indicating products associated with a sport played by the user. Therefore, the user can easily obtain opportunities to purchase a product to suit them.

In addition, the provision information may be generated further on the basis of the user's human relationships. For example, the generator 332 may generate provision information including comparisons with the user's friends or including messages from their friends in cooperation with an SNS or the like. For example, when the sport played by the user is running, the provision information may include information indicating results of a comparison of a travel distance or lap time between the user and their friends. In this manner, the user is provided with provision information generated further on the basis of the user's human relationships. Therefore, the user can keep exercising without getting tired while competing with their friends. This provision information can be output in real time to the user who is exercising. In this case, it is possible to increase the user's motivation while they are exercising.

The process of generating provision information by the generator 332 may be performed by a third party and/or an operator. Examples of the third party include an arbitrary number of SNS operating companies, sports companies, training plan preparation companies, event operating companies, and personal trainers. Examples of the operators include a service operating company for the training support system 1 and a company that manufactures the headset 100.

An exemplary configuration of the server 300 according to the present embodiment has been described above.

3. Operation Processes

Operation processes of the training support system 1 according to the present embodiment are described below. First, an exemplary operation process of the headset 100 according to the present embodiment is described with reference to FIG. 5.

FIG. 5 is a flowchart illustrating an exemplary flow of a provision information output process performed by the headset 100 according to the present embodiment.

First, the sensor unit 110 detects exercise information in step S102 as shown in FIG. 5. For example, the sensor unit 110 converts raw data detected by one of an inertial sensor or a biological sensor into exercise information associated with a sport played by the user. For example, when the sport played by the user is running, the sensor unit 110 detects the distance of travel, the intensity of exercise, a pitch, a stride, a pace, or the like.

Then, in step S104, the control unit 160 controls the communication unit 120 such that it transmits the exercise information detected in the above step S102 to the smartphone 200. The control unit 160 may first allow the storage unit 150 to store the detected exercise information and may then allow the communication unit 120 to transmit the exercise information stored in the storage unit 150.

Then, in step S106, the communication unit 120 receives provision information generated by the server 300 from the smartphone 200.

Then, in step S108, the control unit 160 controls the output unit 130 such that it outputs the provision information received in the above step S106.

An exemplary process of outputting provision information by the headset 100 has been described above. An exemplary process of outputting provision information by the smartphone 200 according to the present embodiment will now be described with reference to FIG. 6.

FIG. 6 is a flowchart illustrating an exemplary flow of a provision information output process performed by the smartphone 200 according to the present embodiment.

First, in step S202, the acquirer 252 acquires exercise information as shown in FIG. 6. For example, the acquirer 252 acquires exercise information from the headset 100 through the communication unit 210.

Then, in step S204, the storage controller 254 allows the server 300 to store the exercise information acquired in the above step S202. For example, the storage controller 254 transmits the exercise information acquired by the acquirer 252 to the server 300 through the communication unit 210 and allows the server 300 to store the exercise information.

Then, the output controller 256 acquires provision information in step S206. For example, the output controller 256 receives provision information, which the server 300 has generated on the basis of a history of exercise information of the user, from the server 300 through the communication unit 210.

Then, the output controller 256 processes the provision information in step S208. For example, the output controller 256 processes a variable part of the provision information generated by the server 300 in accordance with a user instruction.

Then, in step S210, the output controller 256 performs control to output the provision information. The output controller 256 may allow the output unit 220 to output the provision information and may also allow the headset 100 to output the provision information through the communication unit 210.

An exemplary process of outputting provision information by the smartphone 200 has been described above. An overall provision information output procedure of the training support system 1, together with an exemplary user interface (UI) displayed on the smartphone 200, will now be described with reference to FIGS. 7 to 14.

Figure 7:
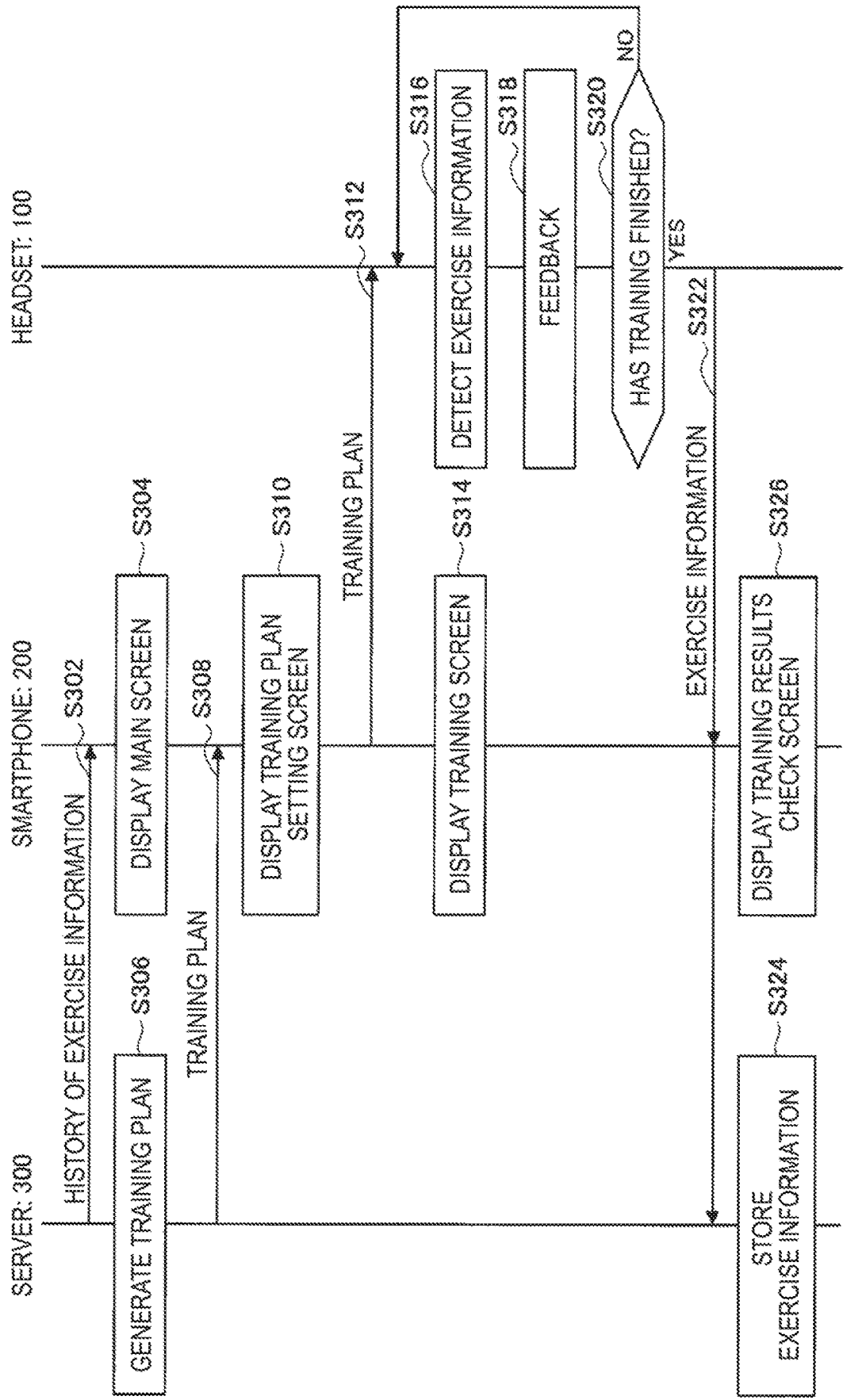
FIG. 7 is a sequence diagram illustrating an exemplary flow of a provision information output process performed by the training support system according to the present embodiment.

FIG. 7 is a sequence diagram illustrating an exemplary flow of a provision information output process performed by the training support system 1 according to the present embodiment. This sequence involves the headset 100, the smartphone 200, and the server 300 as shown in FIG. 7.

First, the server 300 transmits a history of exercise information to the smartphone 200 in step S302. The transmitted history of exercise information is a history of exercise information collected on exercise, which a user wearing the headset 100 has performed in the past, and accumulated in the server 300.

Then, the smartphone 200 displays a main screen in step S304. For example, the smartphone 200 displays, as the main screen, information indicating a record of exercise that the user has performed in the past. An exemplary main screen will now be described below with reference to FIG. 8.

Figure 8:
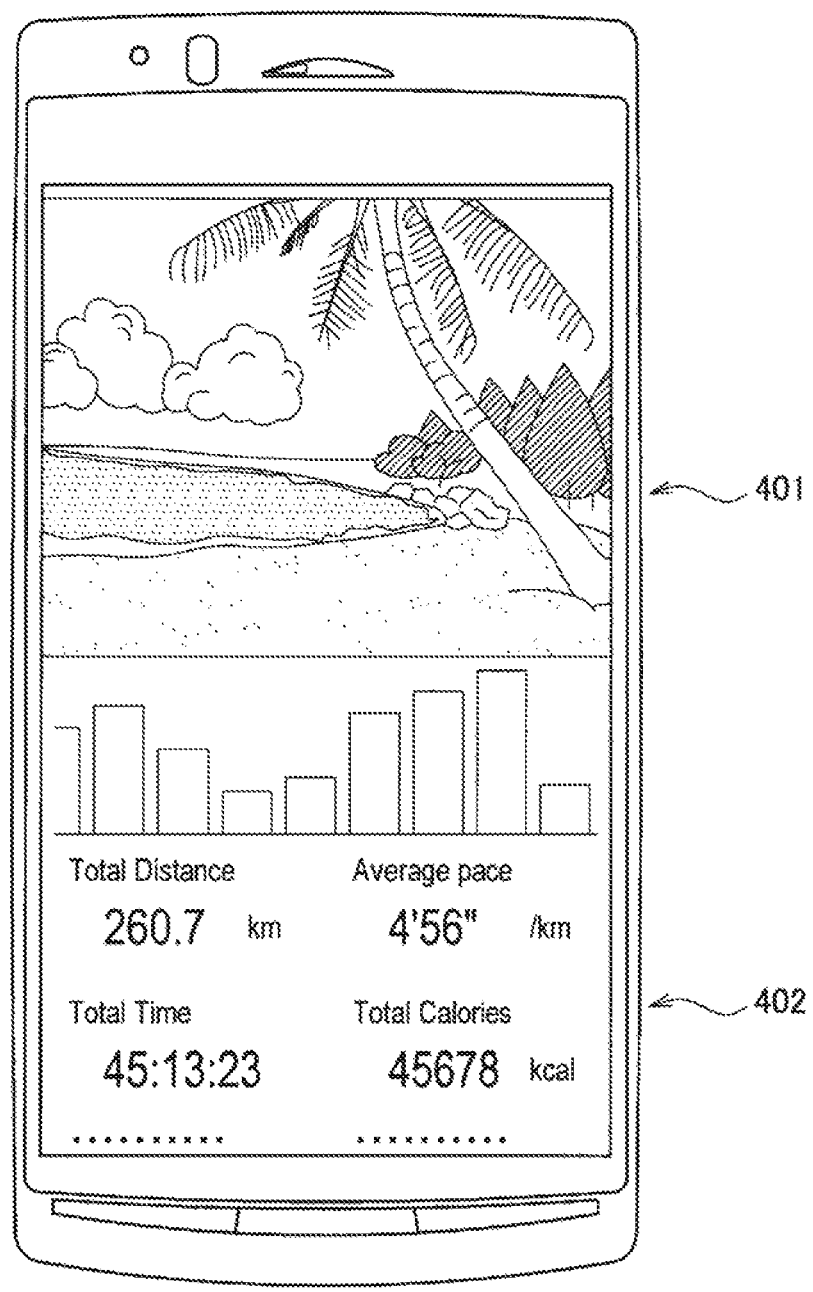
FIG. 8 is a view illustrating an exemplary UI according to the present embodiment.

FIG. 8 is a view illustrating an exemplary UI according to the present embodiment. A record of exercise that the user has performed in the past is displayed on the main screen as shown in FIG. 8. More specifically, a bar chart representing travel distances in chronological order, a total travel distance (Total Distance), a total travel time (Total Time), an average pace per kilometer (Average Pace), total calorie consumption (Total Calories), etc., are displayed on a lower portion 402 of the main screen. In addition, an image associated with exercise that the user has performed in the past is displayed on an upper portion 401 of the main screen. For example, the smartphone 200 may display an image captured at a spot where the highest speed was achieved each time as an impressive scene associated with past exercise. In this case, the user can visually identify a record of exercise that they have performed in the past.

A detailed description of manipulations associated with screen transition is omitted below. The smartphone 200 may perform screen transition in response to a user manipulation or the like as a trigger and may also perform screen transition in response to reception of information from the headset 100 or the server 300 or the like as a trigger.

Then, the server 300 generates one or more training plans as provision information in step S306. Here, the server 300 generates a training plan on the basis of a history of exercise information of the user. The server 300 may also generate a training plan further on the basis of ambient environments (such as a geographical environment, a human environment, and event) of the user. For example, the server 300 adjusts the speed of the training plan in accordance with the user's average or maximum speed in the past or adjusts the intensity of exercise of the training plan in accordance with a time left until the next marathon race is held.

Then, in step S308, the server 300 transmits the one or more training plans generated in the above step S306 to the smartphone 200.

Then, the smartphone 200 displays a training plan setting screen in step S310. For example, the smartphone 200 displays, as the training plan setting screen, a screen that allows the user to select exercise (training) that they are going to perform. Here, the user can set, as a training plan, target values such as a travel time, a travel distance, a pace, and calorie consumption. For example, the smartphone 200 may also display, as the training plan setting screen, information associated with a training plan that was performed in the past or a training plan that is to be performed in the future. The smartphone 200 may also display a screen showing details of each training plan. An exemplary training plan setting screen will now be described below with reference to FIG. 9.

Figure 9:
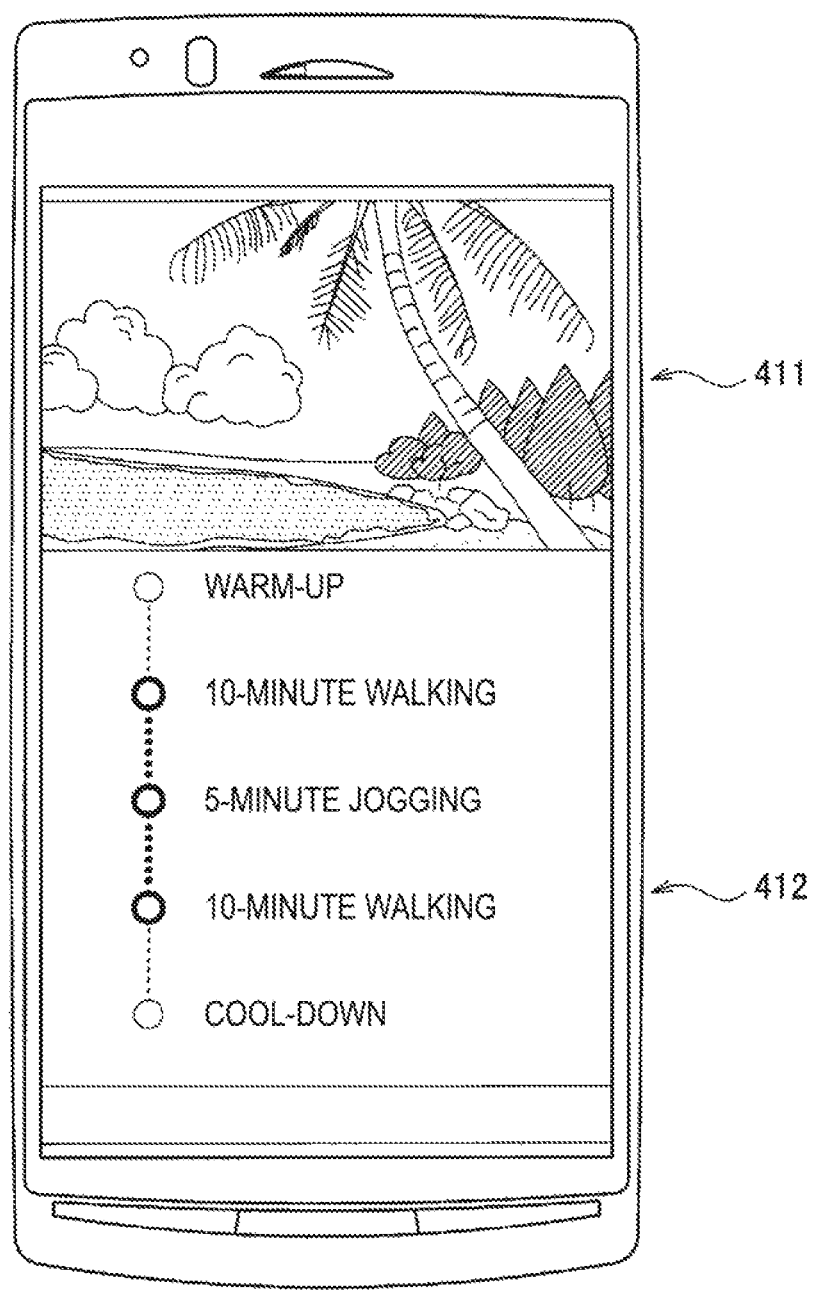
FIG. 9 is a view illustrating an exemplary UI according to the present embodiment.

FIG. 9 is a view illustrating an exemplary UI according to the present embodiment. A plan of training which the user is going to perform is displayed on a training plan setting screen shown in FIG. 9. More specifically, a training plan is displayed on a lower portion 412 of the training plan setting screen. This training plan includes training in the sequential order of warm-up, 10-minute walking, 5-minute jogging, 10-minute walking, and cool-down. An image associated with the training plan is also displayed on an upper portion 411 of the training plan setting screen. Text including information to be noted or the like may also be displayed in association with each training plan.

In addition, the smartphone 200 may display, as the training plan setting screen, a setting screen allowing the user to set the content of exercise information to be output and/or the output timing of the exercise information. On this setting screen, the user can set exercise information, of which they desire to receive feedback while exercising, or the feedback timing of the exercise information. An exemplary training plan setting screen will now be described below with reference to FIG. 10.

Figure 10:
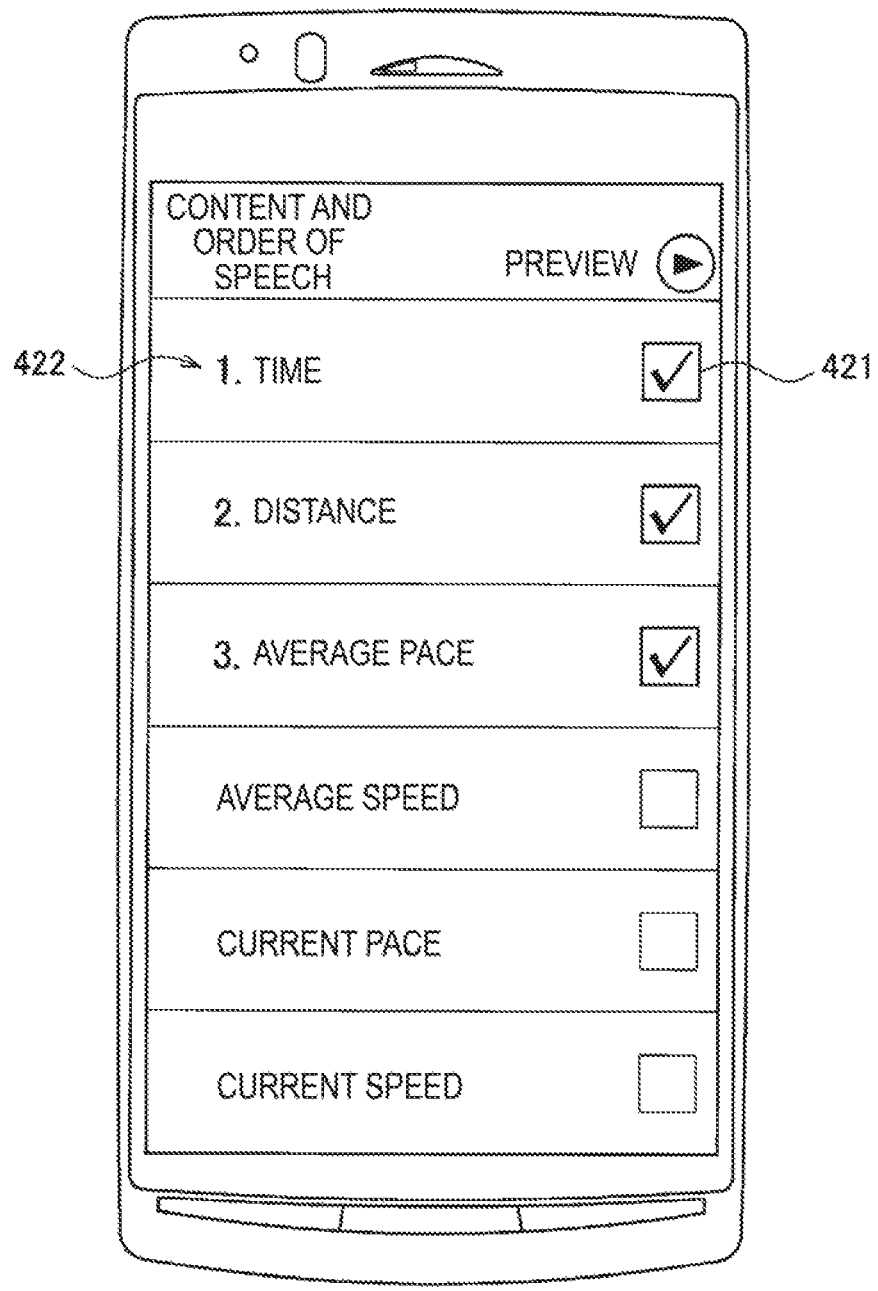
FIG. 10 is a view illustrating an exemplary UI according to the present embodiment.

FIG. 10 is a view illustrating an exemplary UI according to the present embodiment. In the example shown in FIG. 10, a screen for selecting the content of exercise information to be output is displayed as a training plan setting screen to allow selection of a time, a distance, an average pace, an average speed, the current pace, and the current speed. An item is a subject to be audibly output (i.e., spoken) when a corresponding check box 421 is checked and an order of speech 422 can be set for the checked items. In accordance with the setting shown in FIG. 10, the headset 100 outputs the information items in the sequential order of the time, the distance, and the average pace in real time to the user who is exercising.

Then, in step S312, the smartphone 200 transmits the training plan selected in the above step S310 to the headset 100. This initiates training in accordance with the training plan.

The smartphone 200 displays a training screen in step S314. For example, the smartphone 200 may display, as the training screen, a screen for supporting the user who is exercising. Specifically, the smartphone 200 displays, as the training screen, the current position of the user who is traveling or a path taken to get there on a map, displays the progress of the training plan, or displays a controller associated with music playback. An exemplary training screen will now be described below with reference to FIG. 11.

Figure 11:
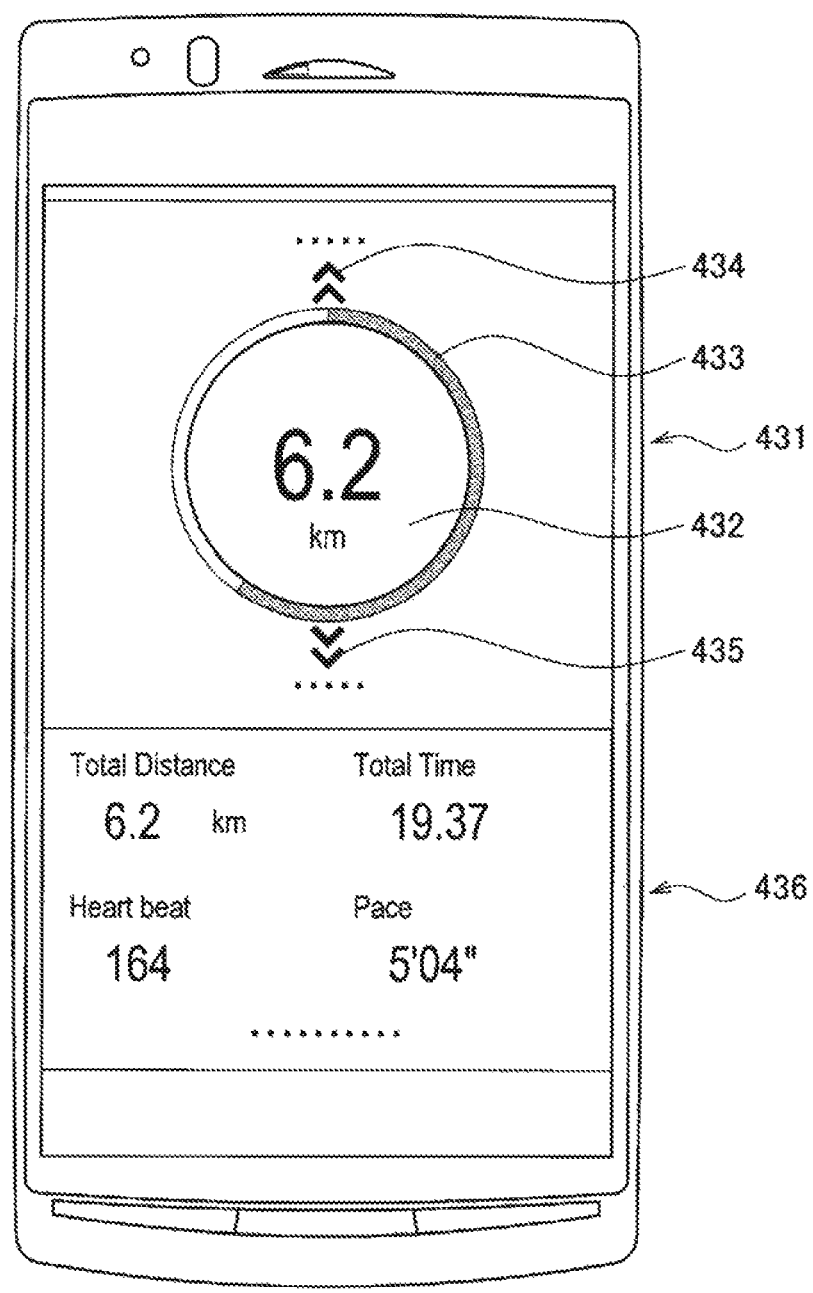
FIG. 11 is a view illustrating an exemplary UI according to the present embodiment.

FIG. 11 is a view illustrating an exemplary UI according to the present embodiment. In the example shown in FIG. 11, a screen showing the progress of a training plan is displayed as the training screen. The progress of the training plan is displayed on an upper portion 431 of the training screen shown in FIG. 11. Specifically, reference numeral 432 denotes the current travel distance as main exercise information of the training plan. Reference numeral 433 represents the current travel distance as the progress in an incomplete ring in a graph which is to be completed with a complete ring when a scheduled travel distance is fully run. Reference numeral 434 denotes a user-manipulatable icon to increase the intensity of exercise of the training plan. Reference numeral 435 denotes a user-manipulatable icon to decrease the intensity of exercise of the training plan. A total travel distance (Total Distance), a total travel time (Total Time), a heart rate (Heart Beat), a pace (Pace), etc., are displayed on a lower portion 436 of the training screen.

On the other hand, the headset 100 detects exercise information first in step S316. For example, the headset 100 detects a heat rate, a travel distance, a speed, an average pace, calorie consumption, or the like. Here, the headset 100 stores the detected exercise information in the storage unit 150.

Then, the headset 100 performs feedback to the user in step S318. For example, the headset 100 audibly outputs the exercise information detected in the above step S316 to the user in real time. Here, the headset 100 may output exercise information that the user has set on the training plan setting screen described above with reference to FIG. 10 at a timing set by the user. In accordance with the setting shown in FIG. 10, the headset 100 audibly outputs the information items detected in the above step S316 in the sequential order of the time, the distance and the average pace in real time to the user who is exercising.

Then, the headset 100 determines whether or not the user has finished training in step S320. For example, the headset 100 makes the determination on the basis of the presence or not of a user instruction to finish training or on the basis of whether or not the training based on the training plan has been finished.

The procedure returns to step S316 upon determining that the user continues training (S320: NO). The smartphone 200 also continues the process of step S314.

On the other hand, upon determining that the user has finished training (S320: YES), the headset 100 transmits exercise information accumulated during the training to the smartphone 200 in step S322. The smartphone 200 relays the received exercise information to the server 300.

Then, the server 300 stores the received exercise information in step S324. This stored exercise information is used in the above step S306 for the next training.

Then, the smartphone 200 displays a training results check screen in step S326. For example, the smartphone 200 may display, as the training results check screen, exercise information such as a total travel distance, a total travel time, and an average pace associated with the current training in text. In addition, the smartphone 200 may display, as the training results check screen, the change with time of a heart rate, a pace, or the like in a graph and may also display a travel path in different colors on a map in accordance with this change with time. Further, the smartphone 200 may display, as the training results check screen, a record of lap times or the like at intervals of a predetermined distance and may also display the recorded spot on the map. The smartphone 200 may also display, as the training results check screen, a result of a comparison of the results of the current training with the past training. The smartphone 200 may also display a history of music played during training as the training results check screen. The smartphone 200 may also display a list of voice memos stored during training as the training results check screen. An exemplary training results check screen will now be described with reference to FIGS. 12 to 14.

Figure 12:
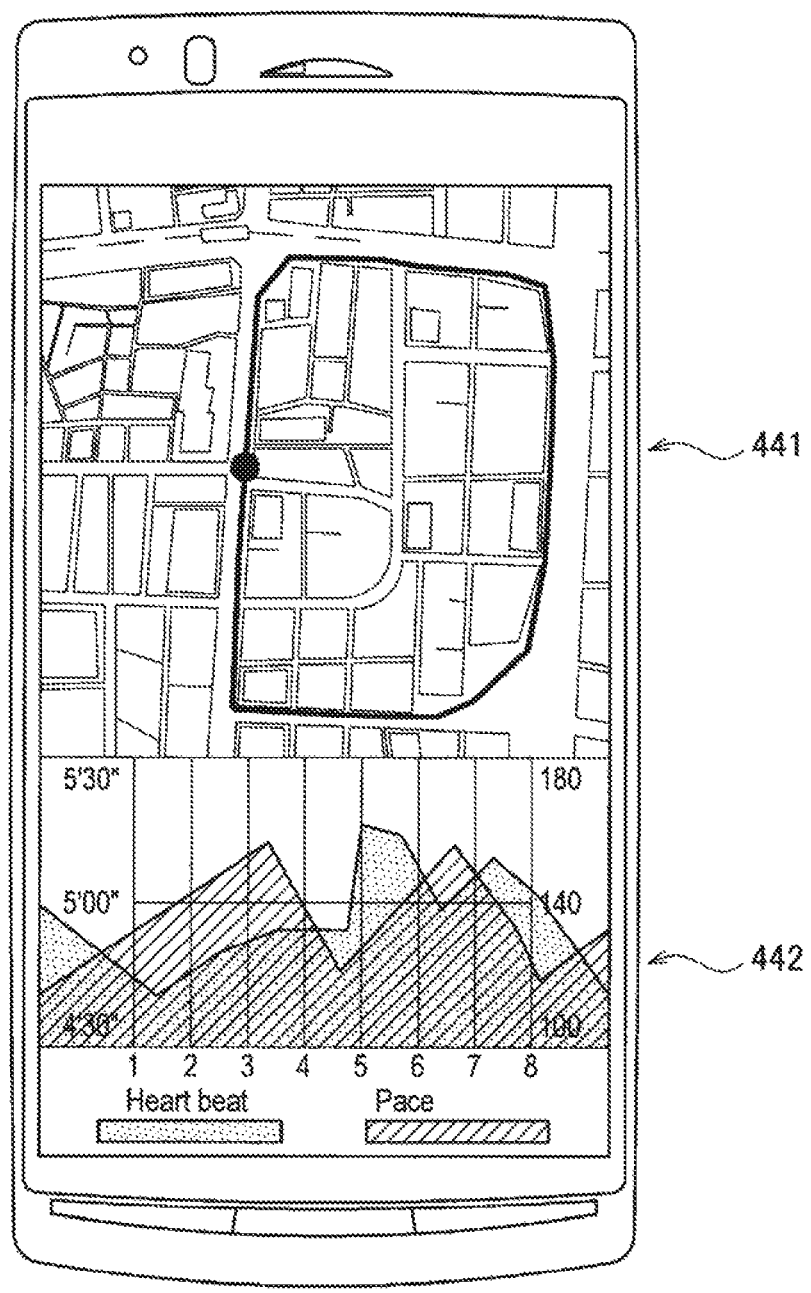
FIG. 12 is a view illustrating an exemplary UI according to the present embodiment.

FIG. 12 is a view illustrating an exemplary UI according to the present embodiment. A travel path is displayed on a map on an upper portion 441 of a training results check screen shown in FIG. 12. The change with time of a heart rate and a pace is displayed in a graph on a lower portion 442 of the training results check screen shown in FIG. 12.

Figure 13:
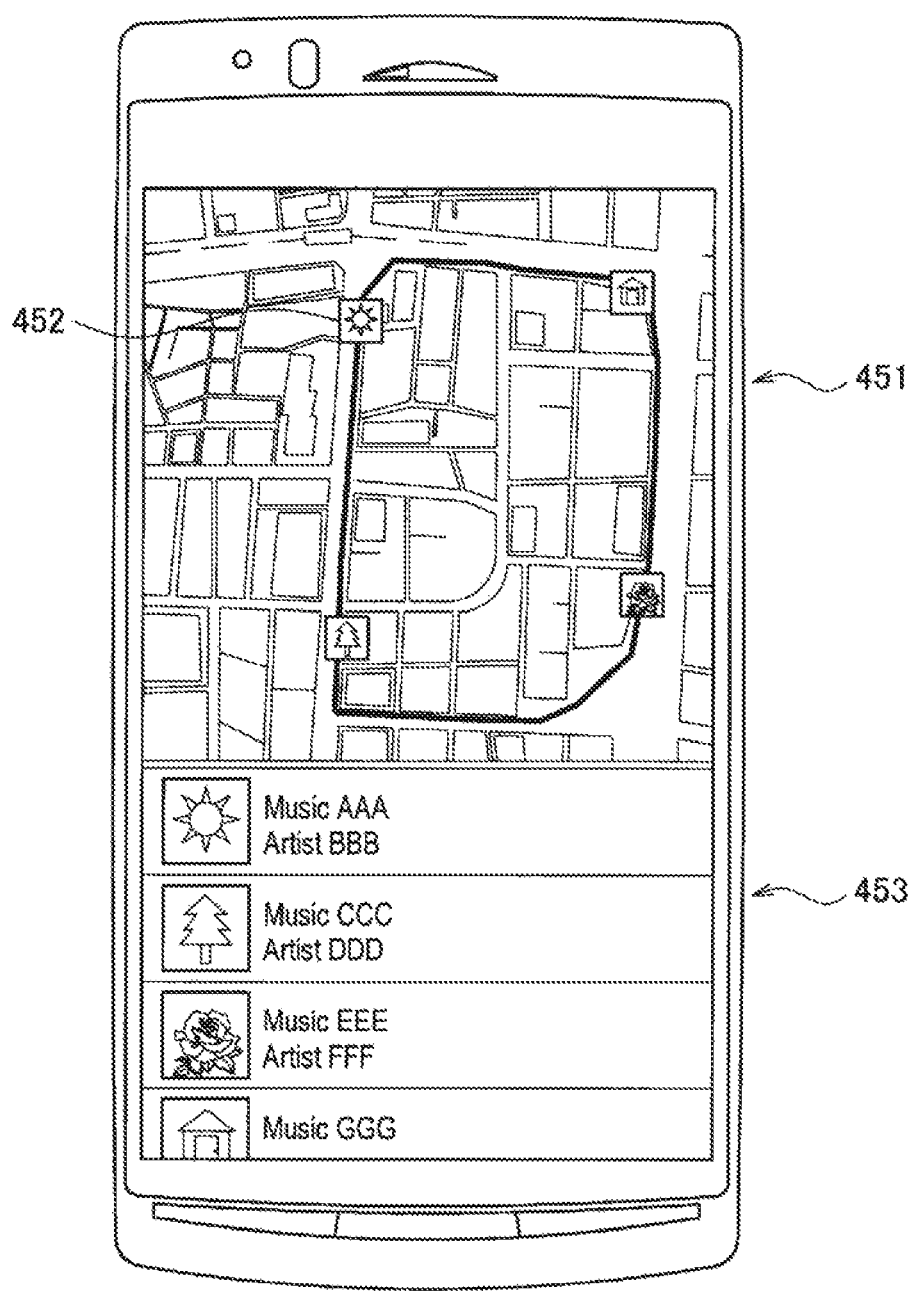
FIG. 13 is a view illustrating an exemplary UI according to the present embodiment.

FIG. 13 is a view illustrating an exemplary UI according to the present embodiment. A travel path is displayed on a map on an upper portion 451 of a training results check screen shown in FIG. 13 with a thumbnail 452 corresponding to a piece of music being displayed at a spot where the piece of music was played. A list of thumbnails, music titles, and artist's names of played music is displayed on a lower portion 453 of the training results check screen.

Figure 14:
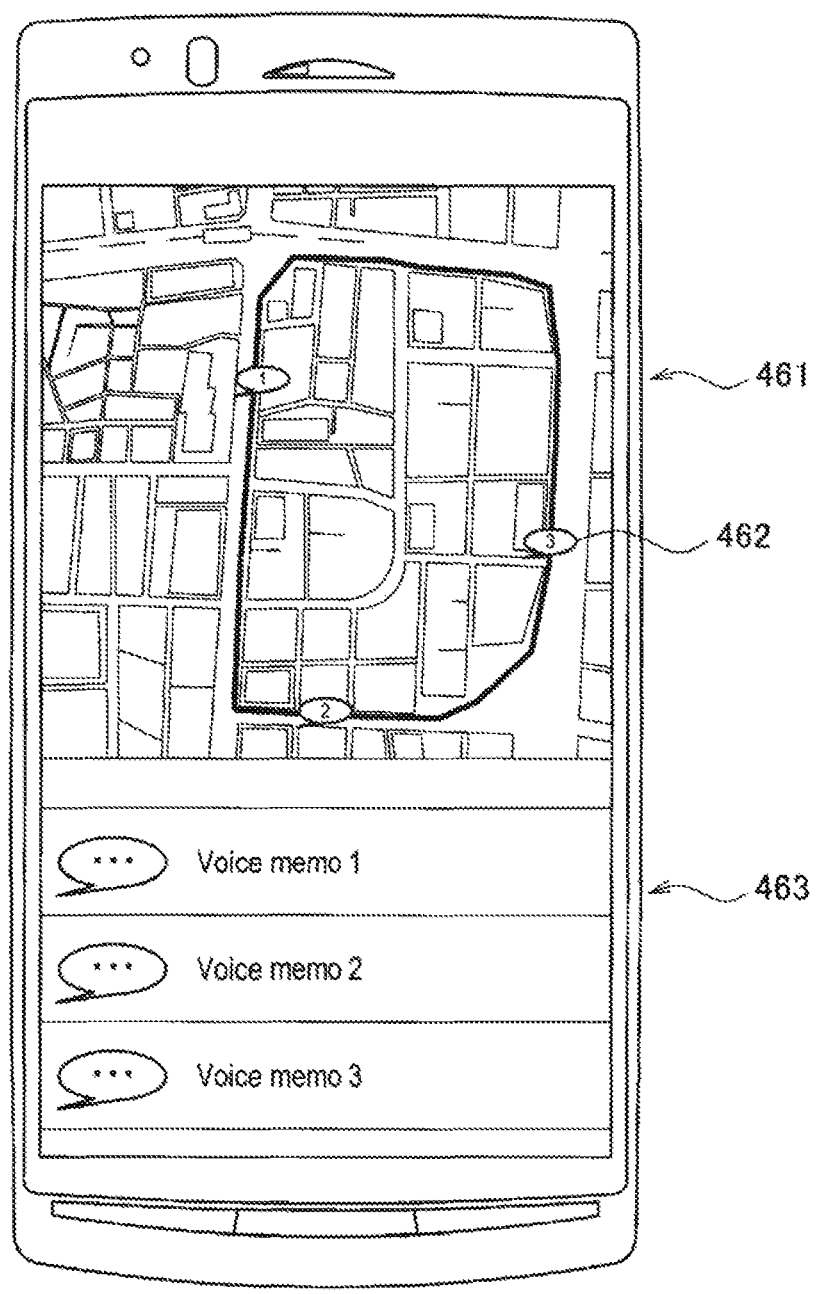
FIG. 14 is a view illustrating an exemplary UI according to the present embodiment.

FIG. 14 is a view illustrating an exemplary UI according to the present embodiment. A travel path is displayed on a map on an upper portion 461 of a training results check screen shown in FIG. 14 with an icon 462 indicating a voice memo being displayed at a spot where the voice memo was stored. A list of stored voice memos is also displayed on a lower portion 463 of the training results check screen. The user can listen to a voice memo by selecting it from the displayed list of voice memos.

An example of the overall provision information output procedure of the training support system 1 has been described above.

4. Hardware Configuration

A hardware configuration of an information processing device according to the present embodiment will now be described with reference to FIGS. 15 to 16.

4-1. First Exemplary Configuration

Figure 15:
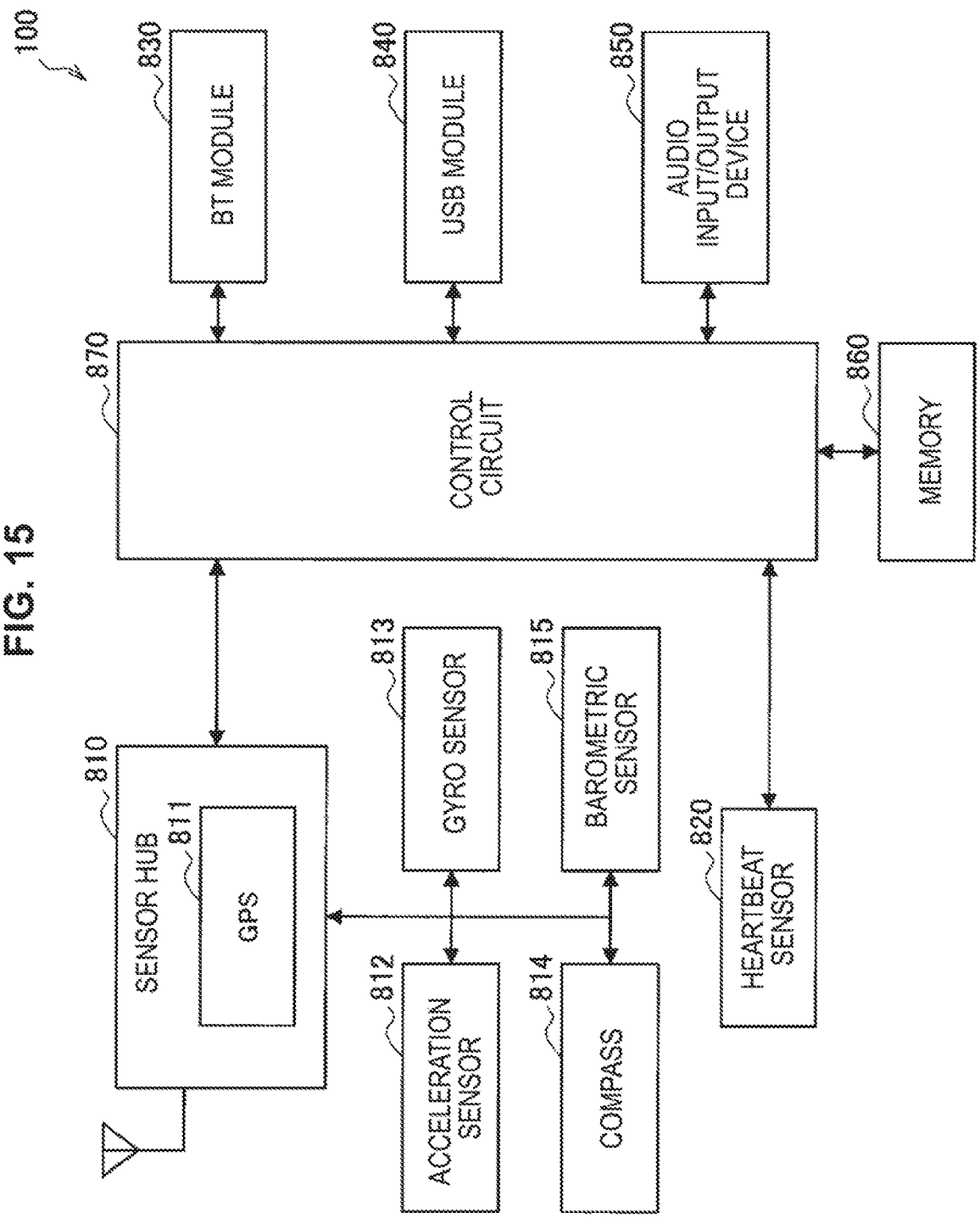
FIG. 15 is a block diagram illustrating an exemplary hardware configuration of an information processing device according to the present embodiment.

FIG. 15 is a block diagram illustrating an exemplary hardware configuration of an information processing device according to the present embodiment. FIG. 15 also illustrates an exemplary hardware configuration of the headset 100 shown in FIG. 2. Information processing by the headset 100 according to the present embodiment is implemented through cooperation of software with hardware described below.

As shown in FIG. 15, the headset 100 has a sensor hub 810 including a GPS 811 therein, an acceleration sensor 812, a gyro sensor 813, a compass 814, an barometric sensor 815, and a heartbeat sensor 820. The headset 100 also has a Bluetooth (registered trademark) (BT) module 830, a universal serial bus (USB) module 840, an audio input/output device 850, a memory 860, and a control circuit 870.

The sensor hub 810 has a function to control one or more sensor devices connected to the sensor hub 810. The acceleration sensor 812, the gyro sensor 813, the compass 814, and the barometric sensor 815 are connected to the sensor hub 810. The sensor hub 810 controls the GPS 811 included therein in the same manner as it controls these sensor devices. The GPS 811 has a function to detect position information by receiving radio waves from GPS satellites. The acceleration sensor 812 has a function to detect acceleration. The gyro sensor 813 has a function to detect an angle and an angular speed. The compass 814 has a function to detect a geographical direction. The barometric sensor 815 has a function to detect an atmospheric pressure and also has a function to detect an altitude from the atmospheric pressure. The sensor hub 810, the GPS 8111, the acceleration sensor 812, the gyro sensor 813, the compass 814, and the barometric sensor 815 may form, for example, the sensor unit 110 shown in FIG. 2. For example, the sensor hub 810 may also have a function to convert raw data of exercise information detected by each sensor into information corresponding to a sport. The sensor hub 810 outputs the information acquired through conversion to the control circuit 870. Of course, the sensor hub 810 may also output the raw data, which has not been converted, to the control circuit 870.

The heartbeat sensor 820 has a function to detect a heart rate. For example, the heartbeat sensor 820 includes a light emitting device such as a light emitting diode (LED) and an image capturing device and may detect the heart rate of a user by exposing a part of the user, which is in contact with the headset 100, such as the user's ear to light and detecting the expansion/contraction states of a blood vessel. The heartbeat sensor 820 may also include an acceleration sensor and may remove noise components of the detected heartbeat using the user's movement detected through the acceleration sensor. The heartbeat sensor 820 may form, for example, the sensor unit 110 shown in FIG. 2. The heartbeat sensor 820 may also be connected to the sensor hub 810 to detect the heart rate on the basis of control by the sensor hub 810. The heartbeat sensor 820 outputs the detected heart rate to the control circuit 870.

The BT module 830 is an interface for performing wireless communication with other devices using Bluetooth. Specifically, the BT module 830 performs pairing with the smartphone 200 and data transmission and reception to and from the smartphone 200 using Bluetooth. For example, the BT module 830 may form the communication unit 120 shown in FIG. 2. The BT module 830 according to the present embodiment receives provision information from the smartphone 200 or transmits exercise information to the smartphone 200.

The USB module 840 is an interface for connection with an external device. The USB module 840 is also a connection port for connection with an external device which can perform data transmission through a USB. Specifically, the USB module 840 is connected to the smartphone 200 to perform data transmission. The USB module 840 may form, for example, the communication unit 120 shown in FIG. 2. The USB module 840 according to the present embodiment is connected to the smartphone 200 to receive a music file from the smartphone 200.

The audio input/output device 850 has a function to receive ambient sound. For example, the audio input/output device 850 includes a microphone. The audio input/output device 850 may have a microphone amplifier circuit that performs a process of amplifying an audio signal acquired through the microphone, an A/D converter, and a signal processing circuit that performs processes such as noise removal and sound source separation on audio data. The audio input/output device 850 outputs the processed audio data to the control circuit 870. The audio input/output device 850 has a function to output audio. For example, the audio input/output device 850 includes a driver unit. The audio input/output device 850 may also have a D/A converter that converts received audio data into an analog audio signal and an amplifier circuit that amplifies an audio signal. The audio input/output device 850 outputs (reproduces) audio data provided from the control circuit 870. The audio input/output device 850 may form the output unit 130 and the input unit 140 shown in FIG. 2.

The memory 860 is a device for data storage formed as an example of the storage unit of the headset 100. The memory 860 is realized, for example, by a magnetic storage device such as an HDD, a semiconductor storage device, an optical storage device or a magneto optical storage device. The memory 860 may also include a storage medium, a recording device that records data in the storage medium, a reading device that reads data from the storage medium, and a deleting device that deletes data recorded in the storage medium. For example, the memory 860 accumulates exercise information (converted data or raw data) output from the sensor hub 810. The memory 860 may form the storage unit 150 shown in FIG. 2.

The control circuit 870 functions as an arithmetic processing unit and a control device and controls the overall internal operation of the headset 100 in accordance with various programs. The control circuit 870 may be realized as a central processing unit (CPU) or a microprocessor and may also have a processing circuit such as a DSP or an ASIC. The control circuit 870 may also include a read only memory (ROM) that stores programs, calculation parameters or the like that are used by the control circuit 870 or a random access memory (RAM) that temporarily stores programs that are executed, parameters that appropriately change during the execution, and the like. The control circuit 870 may form the control unit 160 shown in FIG. 2.

The exemplary hardware configuration in which functions of the headset 100 according to the present embodiment can be implemented has been illustrated above. The respective components described above may be formed of a general purpose member or may be formed of hardware that is specialized for functions of respective components. Therefore, it is possible to appropriately change a hardware configuration to be used in accordance with a technical level when the present embodiment is implemented.

Note that a computer program for implementing the above-described respective functions of the headset 100 according to the present embodiment can be prepared and installed in a PC or the like. In addition, it is possible to provide a computer readable recording medium in which such a computer program is stored. The recording medium includes, for example, a magnetic disk, an optical disc, a magneto optical disc and a flash memory. In addition, the computer program may be delivered through, for example, a network, without using the recording medium.

4-2. Second Exemplary Configuration

Figure 16:
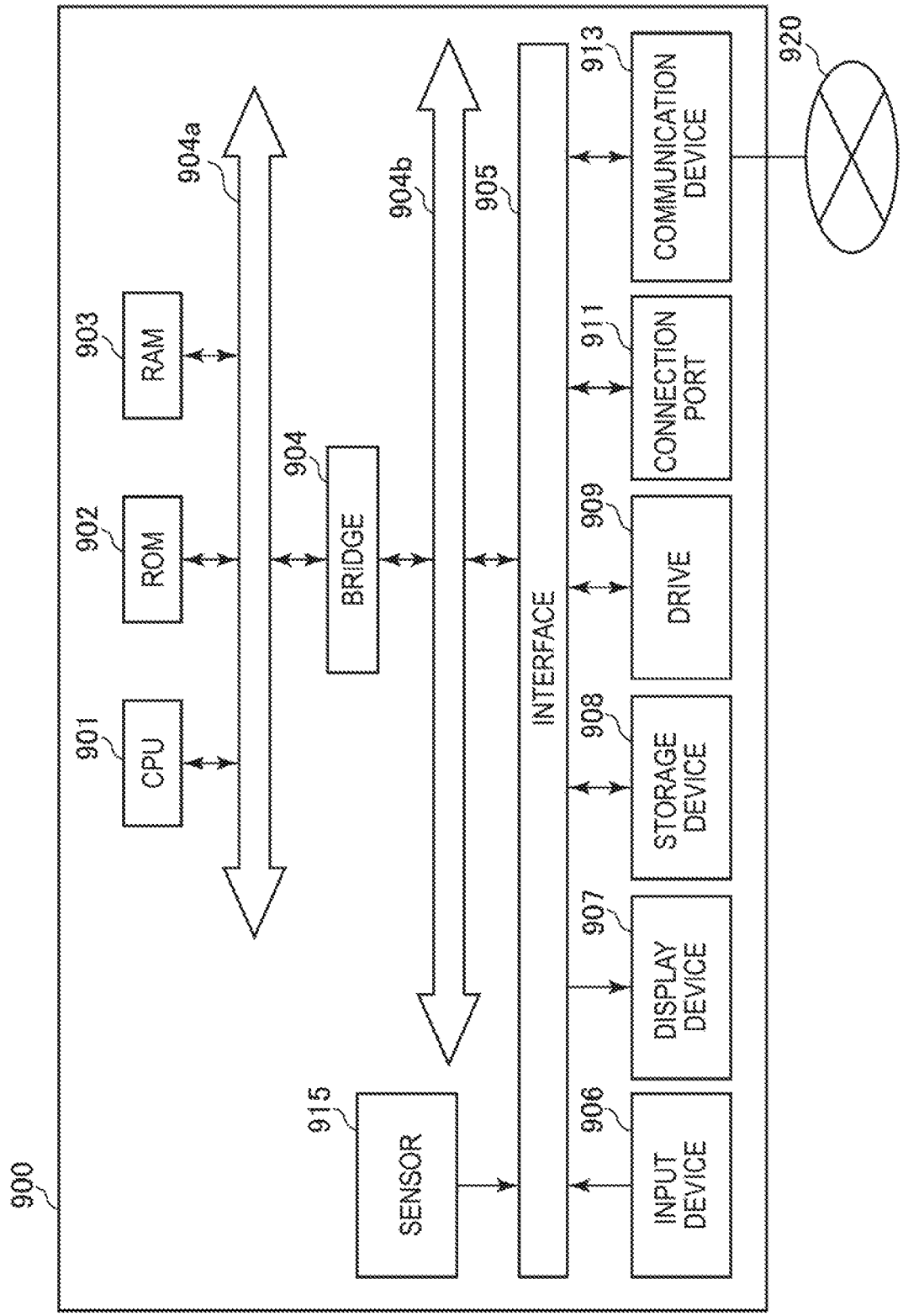
FIG. 16 is a block diagram illustrating an exemplary hardware configuration of an information processing device according to the present embodiment.

FIG. 16 is a block diagram illustrating an exemplary hardware configuration of an information processing device according to the present embodiment. The information processing device 900 shown in FIG. 16 may realize, for example, the smartphone 200 or the server 300, respectively, shown in FIGS. 3 and 4. Information processing by the smartphone 200 or the server 300 according to the present embodiment is implemented through cooperation of software with hardware described below.

As illustrated in FIG. 16, the information processing device 900 includes a central processing unit (CPU) 901, a read only memory (ROM) 902, a random access memory (RAM) 903 and a host bus 904*a*. In addition, the information processing device 900 includes a bridge 904, an external bus 904*b*, an interface 905, an input device 906, an output device 907, a storage device 908, a drive 909, a connection port 911, a communication device 913, and a sensor 915. The information processing device 900 may include a processing circuit such as a DSP or an ASIC instead of or in addition to the CPU 901.

The CPU 901 serves as an arithmetic processing unit and a control device and controls overall operations in the information processing device 900 in accordance with various programs. In addition, the CPU 901 may be a microprocessor. The ROM 902 stores a program, a calculation parameter or the like that is used by the CPU 901. The RAM 903 temporarily stores a program that is used when the CPU 901 is executed, and a parameter that is appropriately changed in the execution. The CPU 901 may form, for example, the control unit 250 illustrated in FIG. 3 and the control unit 330 illustrated in FIG. 4.

The CPU 901, the ROM 902 and the RAM 903 are connected to one another by the host bus 904*a* including a CPU bus. The host bus 904*a* is connected to the external bus 904*b* such as a Peripheral Component Interconnect/Interface (PCI) bus through the bridge 904. Also, it is not necessary to configure the host bus 904*a*, the bridge 904 and the external bus 904*b* separately, but such functions may be implemented in one bus.

The input device 906 is implemented by a device to which information is input by the user, for example, a mouse, a keyboard, a touch panel, a button, a microphone, a switch and a lever. In addition, the input device 906 may be, for example, a remote control device (so-called, a clicker) using infrared rays or other radio waves, or may be an external connection device such as a mobile phone or a PDA corresponding to a manipulation of the information processing device 900. Further, the input device 906 may be formed of an input control circuit or the like that generates an input signal on the basis of information input by the user using, for example, the above input device, and outputs the signal to the CPU 901. The user of the information processing device 900 may input various types of data or instruct a process operation with respect to the information processing device 900 by manipulating the input device 906. The input device 906 may form, for example, the input unit 230 illustrated in FIG. 3.

The output device 907 is formed as a device capable of visually or audibly notifying the user of the acquired information. Such a device includes a display device such as a CRT display device, a liquid crystal display device, a plasma display device, an EL display device and a lamp, an audio output device such as a speaker and a headphone, a printer device or the like. The output device 907 outputs results obtained by various processes performed by, for example, the information processing device 900. Specifically, the display device visually displays results obtained by various processes performed by the information processing device 900 in various forms such as text, an image, a table, or a graph. On the other hand, the audio output device converts an audio signal of reproduced audio data or acoustic data into an analog signal and audibly outputs the result. The display device and the audio output device may form, for example, the output unit 220 illustrated in FIG. 3.

The storage device 908 is a device for data storage formed as an example of the storage unit of the information processing device 900. The storage device 908 is formed of, for example, a magnetic storage device such as an HDD, a semiconductor storage device, an optical storage device or a magneto optical storage device. The storage device 908 may include a storage medium, a recording device configured to record data in the storage medium, a reading device configured to read data from the storage medium, and a deleting device configured to delete data recorded in the storage medium. The storage device 908 stores a program and various types of data executed by the CPU 901 and various types of data acquired from the outside. The storage device 908 may form, for example, the storage unit 240 illustrated in FIG. 3 and the storage unit 320 illustrated in FIG. 4.

The drive 909 is a reader/writer for the storage medium and is built in the information processing device 900 or externally attached. The drive 909 reads information recorded in a removable storage medium such as an installed magnetic disk, optical disc, magneto optical disc, or semiconductor memory, and outputs the information to the RAM 903. In addition, the drive 909 can write information in the removable storage medium.

The connection port 911 is an interface for connection with an external device. For example, the connection port 911 is a connection port for connection with an external device which can perform data transmission through a USB or the like. The connection port 911 may form the communication unit 210 shown in FIG. 3. In the present embodiment, the connection port 911 formed as the communication unit 210 shown in FIG. 3 may transmit a music file to the headset 100.

The communication device 913 is a communication interface formed in a communication device for connection with, for example, a network 920. The communication device 913 is a communication card for, for example, a wired or wireless local area network (LAN), Long Term Evolution (LTE), Bluetooth, or wireless USB (WUSB). In addition, the communication device 913 may be a router for optical communication, a router for Asymmetric Digital Subscriber Line (ADSL), or a modem for various types of communication. The communication device 913 can transmit and receive a signal or the like in compliant with a predetermined protocol, for example, TCP/IP, through, for example, the Internet, or with other communication devices. The communication device 913 may form the communication unit 210 shown in FIG. 3 or the communication unit 310 shown in FIG. 4. In the present embodiment, the communication device 913 formed as the communication unit 210 shown in FIG. 3 may transmit provision information to the headset 100.

Also, the network 920 is a wired or wireless transmission path of information that is transmitted from a device connected to the network 920. For example, the network 920 may include a public network such as the Internet, a telephone line network, and a satellite communication network, various types of local area networks (LANs) including Ethernet (registered trademark), and a wide area network (WAN). In addition, the network 920 may include a dedicated line network such as Internet Protocol-Virtual Private Network (IP-VPN).

Examples of the sensor 915 include various sensors such as an acceleration sensor, a gyro sensor, a geomagnetic sensor, an optical sensor, a sound sensor, a distance measurement sensor, and a force sensor. The sensor 915 acquires information associated with the states of the information processing device 900 such as the orientation, moving speed or the like of the information processing device 900 or information associated with the ambient environment of the information processing device 900 such as the ambient brightness, noise or the like of the information processing device 900. The sensor 915 may also include a GPS sensor that measures the latitude, longitude, and altitude of a device by receiving GPS signals. The smartphone 200 according to the present embodiment may also include, although omitted in FIG. 3, the sensor 915.

The exemplary hardware configuration in which functions of the information processing device 900 according to the present embodiment can be implemented has been illustrated above. The respective components described above may be formed of a general purpose member or may be formed of hardware that is specialized for functions of respective components. Therefore, it is possible to appropriately change a hardware configuration to be used in accordance with a technical level when the present embodiment is implemented.

Note that a computer program for implementing the above-described respective functions of the information processing device 900 according to the present embodiment can be prepared and installed in a PC or the like. In addition, it is possible to provide a computer readable recording medium in which such a computer program is stored. The recording medium includes, for example, a magnetic disk, an optical disc, a magneto optical disc and a flash memory. In addition, the computer program may be delivered through, for example, a network, without using the recording medium.

5. Summary

An embodiment of the present disclosure has been described above in detail with reference to FIGS. 1 to 16. As described above, the training support system 1 according to the present embodiment acquires the user's exercise information and allows the acquired exercise information to be stored and then allows provision information generated on the basis of a history of the stored exercise information to be output. Therefore, the training support system 1 can perform feedback in accordance with the history of exercise of the user. As described above, such feedback may be performed by the headset 100 or may be performed by the smartphone 200. In either case, the user can receive an appropriate feedback in accordance with whether they are in good or bad condition compared to the past exercise history, the degree of improvement, etc. Therefore, the training support system 1 can support the user's continuous exercise while increasing their motivation.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Each device described in this specification may be formed as a single device or all or part thereof may be formed as separate devices. For example, the acquirer 252, the storage controller 254 and the output controller 256 among the exemplary functional components of the smartphone shown in FIG. 3 may be provided in a device such as a server on a cloud connected, via a network or the like, to the output unit 220, the input unit 230 and the storage unit 240. The same applies to the headset 100.

Although the above description has been given assuming that the wearable device 100 is a wearable device such as a headset, a glasses-like device, a contact lens-like device, or a necklace-like device which is typically worn on the user's head or its vicinity, the present technology is not limited to such an example. For example, the wearable device 100 may be realized as a wearable device such as a wristwatch-like device which can be worn on a different part of the body. The wristwatch-like device 100 may perform communication with the server 300 indirectly via the smartphone 200 or may perform direct communication with the server 300. For example, when the wristwatch-like device 100 is provided with a sensor unit 110 including an inertial sensor or a biological sensor which can detect information indicating the user's exercise state, the wristwatch-like device 100 may directly or indirectly transmit the detected exercise information to the server 300. In addition, when the wristwatch-like device 100 is provided with an output unit 130 such as a display that can output information, the wristwatch-like device 100 may directly or indirectly receive provision information generated by the server 300 and provide the received provision information to the user.

Note that it is not necessary for the processing described in this specification with reference to the flowchart to be executed in the order shown in the flowchart. Some processing steps may be performed in parallel. Further, some of additional steps can be adopted, or some processing steps can be omitted.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A program causing a computer to function as:

an acquirer configured to acquire information indicating an exercise state of a user;

a storage controller configured to cause the information indicating the exercise state acquired by the acquirer to be stored; and an output controller configured to cause provision information that is to be provided to the user to be output, the provision information being generated on a basis of a history of the information indicating the exercise state stored by the storage controller.

(2)

The program according to (1), wherein the provision information is generated further on a basis of a sport played by the user.

(3)

The program according to (2), wherein the provision information includes advice about the sport played by the user.

(4)

The program according to (2) or (3), wherein the provision information includes information indicating an event associated with the sport played by the user.

(5)

The program according to any one of (2) to (4), wherein the provision information includes information indicating a product associated with the sport played by the user.

(6)

The program according to any one of (1) to (5), wherein the provision information is generated further on a basis of a human relationship of the use.

(7)

The program according to any one of (1) to (6), wherein the output controller controls a tempo of music that is played in accordance with the exercise state to be aimed at.

(8)

The program according to any one of (1) to (7), wherein the output controller processes the provision information that is to be provided, in accordance with a user instruction.

(9)

The program according to any one of (1) to (8), wherein the information indicating the exercise state is detected by at least one of an inertial sensor or a biological sensor.

(10)

The program according to any one of (1) to (9), wherein the acquirer acquires the information indicating the exercise state from a wearable device that is worn by the user.

(11)

An information processing system including:

a wearable device that is worn by a user;

a server; and a terminal device configured to perform communication with the wearable device and the server, wherein the wearable device includes a sensor unit configured to detect information indicating an exercise state of the user, and an output unit configured to output provision information generated by the server, the server includes a storage unit configured to store information indicating the exercise state, and a generator configured to generate the provision information, which is to be provided to the user, on a basis of a history of the information indicating the exercise state stored in the storage unit, and the terminal device includes an acquirer configured to acquire the information indicating the exercise state detected by the wearable device, a storage controller configured to cause the server to store the information indicating the exercise state acquired by the acquirer, and an output controller configured to cause the output unit to output the provision information generated by the generator.

REFERENCE SIGNS LIST 1 training support system
100 headset
110 sensor unit
120 communication unit
130 output unit
140 input unit
150 storage unit
160 control unit
200 smartphone
210 communication unit
220 output unit
230 input unit
240 storage unit
250 control unit
252 acquirer
254 storage controller
256 output controller
300 server
310 communication unit
320 storage unit
330 control unit
332 generator
810 sensor hub
811 GPS
812 acceleration sensor
813 gyro sensor
814 compass
815 barometric sensor
820 heartbeat sensor
830 BT module
840 USB module
850 audio input/output device
860 memory
870 control circuit

The invention claimed is:

1. A non-transitory computer-readable medium having stored thereon computer-executable instructions that, when executed by a processor, cause the processor to execute operations, the operations comprising:

acquiring, from a user wearable device, first information that indicates an exercise state of a user, wherein the exercise state is detected by one of an inertial sensor or a biological sensor;

transmitting the acquired first information to a server, wherein the acquired first information is stored in the server;

controlling a display screen to output provision information, wherein the provision information is generated by the server based on history information of the exercise state of the user and the detected exercise state of the user, and the provision information includes a result of comparison between history information of a friend of the user and the history information of the user;

controlling the display screen to display an incomplete ring in a graph, wherein the incomplete ring indicates a progress of a distance travelled by the user; and controlling, based on completion of a scheduled travel distance of the user, the display screen to change the display of the incomplete ring to a complete ring.

2. The non-transitory computer-readable medium according to claim 1, wherein the provision information is generated based on a played sport.

3. The non-transitory computer-readable medium according to claim 2, wherein the provision information includes feedback information that corresponds to the played sport.

4. The non-transitory computer-readable medium according to claim 2, wherein the provision information includes second information that indicates an event associated with the played sport.

5. The non-transitory computer-readable medium according to claim 2, wherein the provision information includes third information that indicates a product associated with the played sport.

6. The non-transitory computer-readable medium according to claim 1, wherein the provision information is generated based on a human relationship of the user.

7. The non-transitory computer-readable medium according to claim 1, wherein the operations further comprise controlling a tempo of music, and play of the music is based on a target exercise state of the user.

8. The non-transitory computer-readable medium according to claim 1, wherein the operations further comprise controlling the display screen to output the provision information based on an instruction of the user.

9. An information processing system, comprising:
a user wearable device;
a server; and
a terminal device configured to communicate with the user wearable device and the server, wherein
the user wearable device includes:
a sensor unit configured to detect an exercise state of a user, and
an output unit configured to output provision information,
the server includes:
a storage unit configured to store information that indicates the exercise state, and
a generator configured to generate the provision information based on the detected exercise state of the user and history information of the exercise state of the user, and
the terminal device comprises:
an acquirer configured to acquire the information that indicates the exercise state,
a storage controller configured to transmit the acquired information, and
an output controller configured to:
control a display screen to output the provision information, wherein the provision information includes a result of comparison between history information of a friend of the user and the history information of the user,
control the display screen to display an incomplete ring in a graph, wherein the incomplete ring indicates a progress of a distance travelled by the user, and control, based on completion of a scheduled travel distance of the user, the display screen to change the display of the incomplete ring to a complete ring.

10. A method, comprising:

acquiring, from a user wearable device, information that indicates an exercise state of a user, wherein the exercise state is detected by one of an inertial sensor or a biological sensor;

transmitting the acquired information to a server, wherein the acquired information is stored in the server;

controlling a display screen to output provision information, wherein
the provision information is generated by the server based on history information of the exercise state of the user and the detected exercise state of the user, and
the provision information includes a result of comparison between history information of a friend of the user and the history information of the user;

controlling the display screen to display an incomplete ring in a graph, wherein the incomplete ring indicates a progress of a distance travelled by the user; and controlling, based on completion of a scheduled travel distance of the user, the display screen to change the display of the incomplete ring to a complete ring.

11. The non-transitory computer-readable medium according to claim 1, wherein the provision information includes text information associated with a training plan of the user.

12. The non-transitory computer-readable medium according to claim 1, wherein the operations further comprise controlling the display screen to display a travel path of the user on a map.

13. The non-transitory computer-readable medium according to claim 12, wherein
the operations further comprise controlling the display screen to concurrently display the travel path and a thumbnail that corresponds to a music, and
the thumbnail indicates a spot on the map where the music is played.

14. The non-transitory computer-readable medium according to claim 12, wherein
the operations further comprise controlling the display screen to concurrently display the travel path and a thumbnail that corresponds to a voice memo, and
the thumbnail indicates a spot on the map where the voice memo is stored.

* * * * *